(12) United States Patent
Seth et al.

(10) Patent No.: US 9,402,877 B2
(45) Date of Patent: Aug. 2, 2016

(54) METHODS AND COMPOSITIONS FOR ORAL ADMINISTRATION OF MELANOCORTIN RECEPTOR AGONIST COMPOUNDS

(71) Applicant: XION PHARMACEUTICALS CORPORATION, Roslyn Heights, NY (US)

(72) Inventors: Gaurav Seth, Roslyn Heights, NY (US); Natan Bar-Chama, Cresskil, NJ (US)

(*) Notice: Subject to any disclaimer, the term of this patent is extended or adjusted under 35 U.S.C. 154(b) by 0 days.

(21) Appl. No.: 14/356,146

(22) PCT Filed: Nov. 2, 2012

(86) PCT No.: PCT/US2012/063262
§ 371 (c)(1),
(2) Date: May 2, 2014

(87) PCT Pub. No.: WO2013/067309
PCT Pub. Date: May 10, 2013

(65) Prior Publication Data
US 2015/0037376 A1    Feb. 5, 2015

Related U.S. Application Data

(60) Provisional application No. 61/555,737, filed on Nov. 4, 2011, provisional application No. 61/675,476, filed on Jul. 25, 2012.

(51) Int. Cl.
| | | |
|---|---|---|
| *A61K 38/08* | (2006.01) | |
| *A61K 38/12* | (2006.01) | |
| *A61K 38/10* | (2006.01) | |
| *A61K 45/06* | (2006.01) | |

(52) U.S. Cl.
CPC ............... *A61K 38/12* (2013.01); *A61K 38/08* (2013.01); *A61K 38/10* (2013.01); *A61K 45/06* (2013.01)

(58) Field of Classification Search
CPC ........ A61K 38/12; A61K 38/08; A61K 38/10
USPC ................................................ 514/21.5, 21.6
See application file for complete search history.

(56) References Cited

U.S. PATENT DOCUMENTS

| | | | | | |
|---|---|---|---|---|---|
| 5,122,376 | A * | 6/1992 | Aliverti | ............... | A61K 9/0043 424/405 |
| 5,534,496 | A * | 7/1996 | Lee | ............... | A61K 38/1709 424/434 |
| 5,912,014 | A * | 6/1999 | Stern | ............... | A61K 9/4858 424/426 |
| 6,423,334 | B1 * | 7/2002 | Brayden | ............... | A61K 47/14 424/400 |
| 2004/0260063 | A1 * | 12/2004 | Haskell-Luevano | ... | A61K 38/04 530/350 |
| 2005/0038230 | A1 * | 2/2005 | Sharma | ............... | C07K 5/1008 530/350 |
| 2007/0054843 | A1 | 3/2007 | Yeomans et al. | | |
| 2007/0093420 | A1 | 4/2007 | Yeomans et al. | | |
| 2009/0069242 | A1 * | 3/2009 | Jonassen | ............... | C07K 14/685 514/18.6 |
| 2009/0181880 | A1 | 7/2009 | Yeomans et al. | | |
| 2009/0291900 | A1 | 11/2009 | Yeomans et al. | | |
| 2009/0317377 | A1 | 12/2009 | Yeomans et al. | | |
| 2010/0080797 | A1 | 4/2010 | Yeomans et al. | | |
| 2011/0009341 | A1 | 1/2011 | Sharma et al. | | |
| 2011/0250212 | A1 | 10/2011 | Yeomans et al. | | |
| 2012/0029998 | A1 | 2/2012 | Aversano et al. | | |
| 2012/0220525 | A1 * | 8/2012 | Gruber | ............... | C07K 14/665 514/10.7 |
| 2012/0225831 | A1 * | 9/2012 | Yang | ............... | C07K 14/68 514/21.7 |
| 2012/0322736 | A1 | 12/2012 | Yeomans et al. | | |

FOREIGN PATENT DOCUMENTS

| | | |
|---|---|---|
| AU | 2006282799 A | 3/2007 |
| CA | 2620202 A | 3/2007 |
| CA | 2620364 A | 3/2007 |
| EP | 1928484 A | 6/2008 |
| EP | 2056800 A | 5/2009 |
| EP | 2179741 A | 4/2010 |
| WO | 2007025249 A | 3/2007 |
| WO | 2007025286 A | 3/2007 |

OTHER PUBLICATIONS

Damien Bochelen, "International Search Report and Written Opinion" issued by European Patent Office on Feb. 15, 2013.
Kyeongsoon Park et al., "Oral protein delivery: Current status and future prospect", Reactive & Functional Polymers, Elsevier Science Publishers BV, NL,vol. 71, No. 3, Oct. 3, 2010, pp. 280-287.
Lee et al., "Protease inhibitors and penetration enhancers as approaches to modify peptide absorption", Journal of Controlled Release, Elsevier, Amsterdam, NL,vol. 13, No. 2-3, Aug. 1, 1990, pp. 213-223, XP025497101.
Maria Dorly Del Curto et al., "Oral delivery system for two-pulse colonic release of protein drugs and protease inhibitor/absorption enhancer compounds",Journal of Pharmaceutical Sciences, vol. 100, No. 8, Aug. 1, 2011, pp. 3251-3259.

* cited by examiner

*Primary Examiner* — David Lukton
(74) *Attorney, Agent, or Firm* — LeonardPatel PC

(57) ABSTRACT

Methods and compositions for oral administration of melanocortin receptor agonist compounds are disclosed herein. Methods and compositions for oral administration of melanocortin receptor agonist compounds are provided for treatment of sexual dysfunction, including male sexual dysfunction and female sexual dysfunction. Methods and compositions for oral administration of melanocortin receptor agonist compounds are provided for treatment of metabolic syndrome, obesity and/or diabetes. In some embodiments, a pharmaceutical composition comprising a peptide-based melanocortin receptor agonist, a protease inhibitor, an absorption enhancer is administered orally.

2 Claims, 1 Drawing Sheet

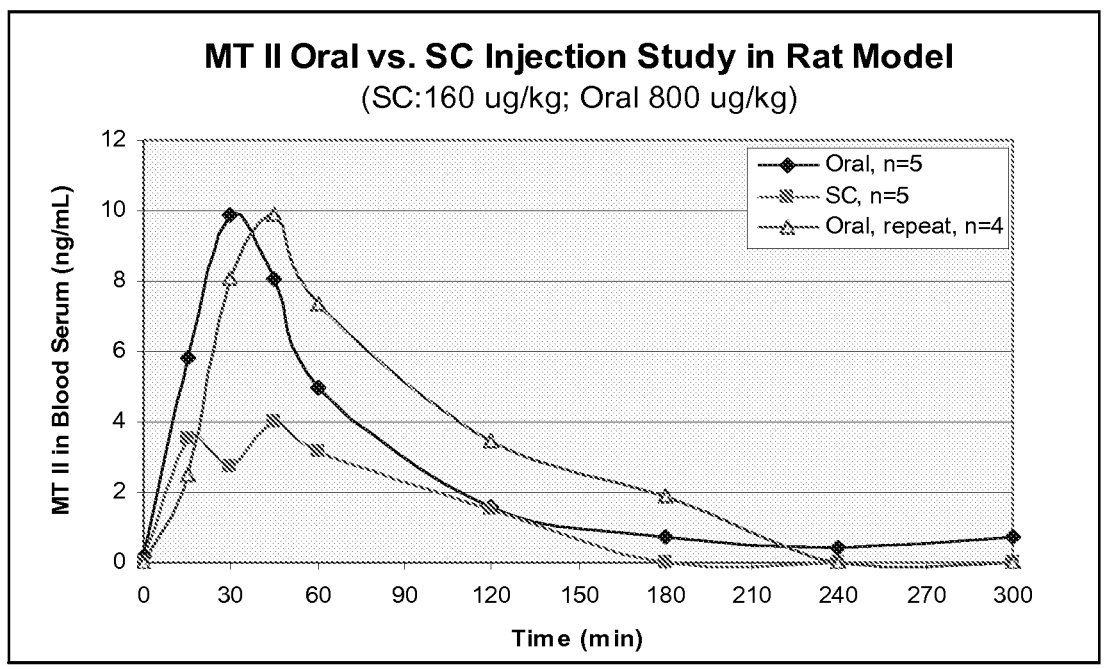

METHODS AND COMPOSITIONS FOR ORAL ADMINISTRATION OF MELANOCORTIN RECEPTOR AGONIST COMPOUNDS

RELATED APPLICATIONS

This application claims the benefit of and priority to U.S. Provisional Application Ser. No. 61/555,737, filed Nov. 4, 2011, and to U.S. Provisional Application Ser. No. 61/675,476, filed Jul. 25, 2012, the entirety of these applications are hereby incorporated herein by reference.

FIELD

The presently disclosed embodiments relate to methods and compositions for oral administration of melanocortin receptor agonist compounds. More particularly, the presently disclosed embodiments relate to methods and compositions for the treatment of melanocortin receptor-mediated disorders including sexual dysfunction, metabolic syndrome, diabetes, obesity and other conditions and diseases.

BACKGROUND

The melanocortin receptors (MC-receptors) belong to the class of G-protein coupled receptors which are all built from a single polypeptide forming seven transmembrane domains. The melanocortin receptors are linked to a variety of physiological actions that are thought to be mediated by distinct subtypes of the MC-receptors. The melanocortin receptor's signaling is mainly mediated via cAMP but also other signal transduction pathways are known. To date, five receptors types, termed MC1-R, MC2-R, MC3-R, MC4-R and MC5-R, have been described. Melanocortin-1 receptors (MC1-R) are expressed on normal human melanocytes and melanoma cells, melanocortin-2 receptors (MC2-R) for ACTH (adrenocorticotropin) are expressed in cells of the adrenal gland, melanocortin-3 and melanocortin-4 receptors (MC3-R and MC4-R) are expressed primarily in cells in the hypothalamus, mid-brain and brainstem, and melanocortin-5 receptors (MC5-R) are expressed in a wide distribution of peripheral tissues.

In general, compounds specific for MC3-R, MC4-R or MC5-R are believed to be useful in regulation of energy homeostasis, including use as agents for attenuating food intake and body weight gain, in treatment of cachexia, in treatment of anorexia, as a weight gain aid, in treatment of obesity, and in other treatment of other food intake and metabolism-related purposes. Compounds specific for MC3-R and MC4-R, among other melanocortin receptors, can be used to regulate blood pressure, heart rate and other neurophysiologic parameters. MC4-R antagonists can be used in the treatment of anxiety/depression, pain, and addiction to drugs of abuse. However, in many cases, it is not entirely clear which of the subtypes is responsible for the effect. Melanocyte-stimulating hormones (referred to as MSH) are known agonist of the melanocortin receptors. MSH are a class of peptide hormones including ACTH, α-MSH, β-MSH and γ-MSH. MSHs are believed to affect many different processes such as motivation, learning, memory, behavior (including feeding and sexual), inflammation (including immunostimulatory and immunosuppressive), body temperature, pain perception, blood pressure, heart rate, vascular tone, brain blood flow, trophic effects in different organs, nerve growth, placental development, endocrine and exocrine functions, aldosterone synthesis and release, thyroxin release, spermatogenesis, ovarian weight, prolactin and FSH secretion, effects on other organs, uterine bleeding in women, sebum and pheromone secretion, blood glucose levels, intrauterine fetal growth, as well as other events surrounding parturition and natriuresis as well as inducing natriuresis. MC4-R agonists are believed to be useful for treating sexual dysfunction, for decreasing the body weight and for treatment of depression and related disorders.

There remains a significant need for pharmaceutical compositions and methods of orally administering pharmaceutical compositions comprising peptide-based melanocortin receptor agonists to treat a various melanocortin receptor-mediated diseases. More particularly, there is significant need for pharmaceutical compositions and methods of orally administering pharmaceutical compositions comprising peptide-based melanocortin receptor agonists to treat various melanocortin receptor-mediated diseases with substantially reduced incidence of undesirable side effects.

SUMMARY

The presently disclosed embodiments relate to a method for oral administration of a melanocortin receptor agonist to a subject in need thereof comprising administering orally to the subject a pharmaceutical composition comprising the melanocortin receptor agonist, a protease inhibitor, and an absorption enhancer wherein the absorption enhancer enhances the absorption of the melanocortin receptor through a gastrointestinal mucosal barrier.

The presently disclosed embodiments relate to pharmaceutical compositions comprising the melanocortin receptor agonist, a protease inhibitor, and an absorption enhancer wherein the absorption enhancer enhances the absorption of the melanocortin receptor through a gastrointestinal mucosal barrier. In some embodiments, the pharmaceutical composition can be administered orally to a subject in need thereof to treat sexual dysfunction. Yet in other embodiments, the pharmaceutical composition can be administered orally to a subject in need thereof to treat metabolic syndrome, diabetes, obesity, or any combination thereof.

The presently disclosed embodiments relate to a method of treating sexual dysfunction in a subject, comprising administering orally to the subject a pharmaceutical composition comprising a melanocortin receptor agonist, a protease inhibitor, and an absorption enhancer wherein the absorption enhancer enhances the absorption of the melanocortin receptor through an intestinal mucosal barrier of the subject.

In some embodiments, the pharmaceutical composition further comprises a compound that induce erectile activity. The compound can be selected from the group including phosphodiesterase 5 inhibitor, testosterone, prostaglandin, luteinizing hormone, human chorionic gonadotropin and combinations thereof.

In some embodiments, the pharmaceutical composition further comprises a compound selected form the group of selective androgen receptor modulator, selective estrogen receptor modulator or combinations thereof. The selective androgen receptor modulator can be selected from the group of flutamide, nilutamide, zanoterone, bicalutamide, and combinations thereof.

The selective estrogen receptor modulator can be selected from the group of tamoxifen, 4-hydroxy tamoxifen, raloxifene, droloxifene, toremifene, centchroman, idoxifene, (−)-cis-6-phenyl-5-[-4-(2-pyrrolidin-1-yl-ethoxy)-phenyl]-5,6,7,8-tetrahy-dro-napththalene-2-ol, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof, pharmaceutically acceptable salts, N-oxides, esters, and quaternary ammonium salts thereof. The phosphodiesterase 5 inhibitor can be selected form the group of 1-[[3-(6,7-dihydro-1-methyl-7-oxo-3-propyl-1-H-pyrazolo[4,3-d]pyrimidin-5-yl]-4-ethoxyphenyl]sufonyl)-4-methylpiperazine citrate and pharmaceutical acceptable salts. In some embodiments, the phosphodiesterase inhibitors is selected from the group of avanafil, lodenafil, mirodenafil, tadalafil, vardenafil, udenafil, sildenafil citrate and pharmaceutical acceptable salts.

The presently disclosed embodiments relate to a method of treating metabolic syndrome, diabetes, obesity, or any combination thereof in a subject, the method comprising administering orally to the subject a pharmaceutical composition comprising a melanocortin receptor agonist, a protease inhibitor, and an absorption enhancer wherein the absorption enhancer enhances the absorption of the melanocortin receptor through an intestinal mucosal barrier of the subject and wherein the subject has metabolic syndrome, diabetes, obesity or any combination thereof.

In some embodiments, the pharmaceutical composition further comprises at least one compound having a therapeutic effect on metabolic syndrome, diabetes, obesity or any combination thereof.

In some embodiments, compound is selected from the group including leptin, Neuropeptide Y (NPY), Agouti-related peptide (AgRP) antagonists, compounds useful in the treatment of diabetes, metabolic syndrome, obesity or any combination thereof.

In some embodiments, the melanocortin receptor agonist is a peptide-based melanocortin receptor agonist. The peptide-based melanocortin receptor agonist can be linear or cyclic. In some embodiments, the peptide-based melanocortin receptor agonist is α-MSH$_{(4-10)}$ (SEQ ID NO. 2), α-MSH$_{(4-11)}$ (SEQ ID NO. 128), α-MSH$_{(4-10)}$ (SEQ ID NO. 129), α-MSH$_{(4-9)}$ (SEQ ID NO. 130), α-MSH$_{(5-13)}$ (SEQ ID No. 131) analog or α-MSH$_{(1-13)}$ (SEQ ID NO. 132), analog thereof, pharmaceutical salts thereof or combinations thereof, pharmaceutical salts thereof or combinations thereof. The peptide-based melanocortin receptor agonist can comprise Nle at position 4 and/or D-Phe at position 7. The peptide-based melanocortin receptor agonist may comprise at least one intramolecular disulfide bond. In some embodiments, the peptide-based melanocortin receptor agonist may be deaminated. or acetylated.

In some embodiments, the peptide-based melanocortin receptor agonist can be selected from the group of Ac-Ser-Tyr-Ser-Met-Glu-His-Phe-Arg-Trp-Gly-Lys-Pro-Val-NH$_2$ (SEQ ID NO. 1), Ac-Ser-Tyr-Ser-Met-Glu-His-D-Phe-Arg-Trp-Gly-Lys-Pro-Val-NH$_2$ (SEQ ID NO. 6), Ac-Nle-Asp-His-D-Phe-Arg-Trp-Lys-NH$_2$ (SEQ ID NO. 9), Ac-Ser-Tyr-Ser-Nle-Glu-His-D-Phe-Arg-Trp-Lys-Gly-Pro-Val-NH$_2$ (SEQ ID NO. 48), Ac-Ser-Tyr-Ser-Nle-Asp-His-D-Phe-Arg-Trp-Lys-Gly-Pro-Val-NH$_2$ (SEQ ID NO. 49), Ac-Nle-Glu-His-D-Phe-Arg-Trp-Lys-Gly-Pro-Val-NH$_2$ (SEQ ID NO. 50), Ac-Nle-Asp-His-D-Phe-Arg-Trp-Gly-NH$_2$ (SEQ ID NO. 51), Ac-Nle-Asp-His-D-Phe-Arg-Trp-Lys-NH$_2$ (SEQ ID NO. 52), Ac-Nle-Asp-His-D-Phe-Arg-Trp-Orn-NH$_2$ (SEQ ID NO. 53), Ac-Nle-Glu-His-D-Phe-Arg-Trp-Orn-NH$_2$ (SEQ ID NO. 54), Ac-Nle-Glu-His-D-Phe-Arg-Trp-Dbu-NH$_2$ (SEQ ID NO. 55), Ac-Nle-Asp-His-D-Phe-Arg-Trp-Dbu-NH$_2$ (SEQ ID NO. 56), Ac-Nle-Asp-His-D-Phe-Arg-Trp-Dpr-NH$_2$ (SEQ ID NO. 57), Ac-Nle-Asp-His-D-Phe-Arg-Trp-Dbu-NH$_2$ (SEQ ID NO. 57), Ac-Nle-Glu-His-D-Phe-Arg-Trp-Dbu-NH$_2$ (SEQ ID NO. 58), analogs thereof, pharmaceutical salts thereof or combinations thereof. In some embodiments, the linear peptide-based melanocortin receptor agonist comprises an hydroxyl group at its carboxyl terminus. In some embodiment, the peptide-based melanocortin receptor agonist has the amino acid sequence AA$_1$-Nle-AA$_2$-His-AA$_3$-Arg-Trp-AA$_4$-AA$_5$ (SEQ ID NO. 59) wherein AA$_1$ is selected from the group of Ac-Ser, Tyr-Ser and Ac, wherein AA$_2$ is selected from the group of amino acid residues consisting of Glu and Asp, wherein AA$_3$ is selected from the group of amino acid residues consisting of D-Phe and Phe, Arg, Trp, wherein AA$_4$ is selected from the group of amino acid residues consisting of Lys, Gly, Orn, Dbu, Dpr and wherein AA$_5$ is selected from the group of amino acid residues consisting of OH, NH$_2$, Gly-Val,-Pro-NH$_2$, and Gly-Val,-Pro-OH, wherein Dbu is 2,4 diaminobutyric acid and Dpr is 2,3 diaminopropionic acid.

In some embodiments, the cyclic peptide-based melanocortin receptor agonist can be selected from the group Ac-Nle-cyclo(Asp-His-D-Phe-Arg-Trp-Lys)-NH$_2$ (SEQ ID NO. 91), Ac-Nle-cyclo(Asp-His-D-Phe-Arg-Trp-Lys)-Gly-NH$_2$ (SEQ ID NO. 92), Ac-Nle-cyclo(Asp-His-D-Phe-Arg-Trp-Lys)-Gly-Pro-NH$_2$ (SEQ ID NO. 93), Ac-Ser-Tyr-Ser-Nle-cyclo(Asp-His-D-Phe-Arg-Trp-Lys)-NH$_2$ (SEQ ID NO. 94), Ac-Ser-Nle-cyclo(Asp-His-D-Phe-Arg-Trp-Lys)-NH$_2$ (SEQ ID NO. 95), Ac-Ser-Tyr-Ser-cyclo-(Cyst-Glu-His-D-Phe-Arg-Trp-Cys)-Lys-Pro-Val-NH$_2$ (SEQ ID NO. 96), Ac-Nle-Asp-His-D-Phe-Arg-Trp-Lys)-NH$_2$ (SEQ ID NO. 97), analogs thereof, pharmaceutical salts thereof or combinations thereof. In some embodiments, the cyclic peptide-based melanocortin receptor agonist comprises an hydroxyl group at its carboxyl terminus.

In some embodiments, the cyclic peptide-based melanocortin receptor agonist can be selected from the group of Ac-cyclo(Cys$^4$,Cys$^{10}$)-α-MSH$_{(1-13)}$-NH$_2$ (SEQ ID NO. 101), Ac-cyclo(Cys$^4$,Cys$^{10}$)-α-MSH$_{(4-13)}$-NH$_2$ (SEQ ID NO. 62), Ac-cyclo(Cys$^4$-D-Phe$^7$-Cys$^{10}$)-α-MSH$_{(4-13)}$-NH$_2$ (SEQ ID NO. 102), Ac-cyclo(Cys$^4$,Cys$^{10}$)-α-MSH$_{(4-12)}$-NH$_2$ (SEQ ID NO. 103), Ac-cyclo(Cys$^4$-D-Phe$^7$-Cys$^{10}$)-α-MSH$_{(4-12)}$-NH$_2$ (SEQ ID NO. 104), Ac-cyclo(Cys$^4$,Cys$^{10}$)-α-MSH$_{(4-11)}$-NH$_2$ (SEQ ID NO. 105), Ac-cyclo(Cys$^4$-D-Phe$^7$-Cys$^{10}$)-α-MSH$_{(4-11)}$-NH$_2$ (SEQ ID NO. 106), Ac-cyclo(Cys$^4$,Cys$^{10}$)-α-MSH$_{(4-10)}$-NH$_2$ (SEQ ID NO. 107), Ac-cyclo(Cys$^4$-D-Phe$^7$-Cys$^{10}$)-α-MSH$_{(4-10)}$-NH$_2$ (SEQ ID NO. 108), Ac-cyclo(Cys$^4$-D-Phe$^7$-Cys$^{10}$)-α-MSH$_{(4-11)}$-NH$_2$ (SEQ ID NO. 109), cyclo(Mpa$^4$, Cys$^{10}$)-α-MSH$_{(4-13)}$-NH$_2$ (SEQ ID NO. 110), cyclo(Maa$^4$,Cys$^{10}$)-α-MSH$_{(4-13)}$-NH$_2$ (SEQ ID NO. 111), Ac-cyclo(Hcy$^4$,Cys$^{10}$)-α-MSH$_{(4-13)}$-NH$_2$ (SEQ ID NO. 112), analogs thereof, pharmaceutical salts thereof or combination thereof, wherein Maa indicates 2-Mercaptoacetic acid, Mpa indicates 3-Mercaptopropionic acid; and Hcy indicates Homocystein.

In some embodiments, the absorption enhancer is N-(8-[2-hydroxybenzoyl]amino)caprylate (SNAC), Sodium N-(10-[2-hydroxybenzoyl]amino)decanoate (SNAD), pharmaceutical salts thereof or a combination thereof. In some embodiments, the absorption enhancer is a bile acid or alkali metal salt thereof.

In some embodiments, the protease inhibitor is a serpin, a suicide inhibitor, a transition state inhibitor, a protein protease inhibitor, a chelating agent, a Cysteine protease inhibitor, a Threonine protease inhibitor, an Aspartic protease inhibitor, a trypsine inhibitor, a metalloprotease inhibitor or a combination thereof. The trypsin inhibitor can be Lima bean trypsin inhibitor, Aprotinin, soy bean trypsin inhibitor (SEM), Ovomucoid or combination thereof.

In some embodiments, the pharmaceutical composition comprises an omega-3 fatty acid. In some embodiments, the pharmaceutical composition comprises EDTA or a salt thereof. In some embodiments, the pharmaceutical composition comprises an antiemetic compound.

In some embodiments, the pharmaceutical composition further comprises a coating that inhibits digestion of the composition in a stomach of a subject. The coating can be an enteric coating, or gelatin coating. In some embodiments, the coating can enhance dissolution of the pharmaceutical composition in the stomach.

DESCRIPTION OF THE SEQUENCE LISTING

SEQ ID No. 1 is an amino acid sequence of α-MSH$_{(1-13)}$.
SEQ ID No. 2 is an amino acid sequence of α-MSH$_{(4-13)}$.
SEQ ID No. 3 is an amino acid sequence of α-MSH$_{(4-10)}$.
SEQ ID No. 4 is an amino acid sequence of α-MSH[D-Phe]$_{(4-10)}$.
SEQ ID No. 5 is an amino acid sequence of a modified α-MSH$_{(4-13)}$.
SEQ ID No. 6 is an amino acid sequence of α-MSH[D-Phe$^7$]$_{(4-13)}$.
SEQ ID No. 7 is an amino acid sequence of a modified α-MSH[D-Phe$^7$]$_{(4-13)}$.
SEQ ID No. 8 is an amino acid sequence of a modified α-MSH$_{(4-13)}$.
SEQ ID No. 9 is an amino acid sequence of a modified α-MSH[D-Phe]$_{(4-10)}$.
SEQ ID No. 10 is an amino acid sequence of a modified α-MSH[D-Phe]$_{(4-10)}$.
SEQ ID No. 11 is an amino acid sequence of a α-MSH$_{(4-10)}$.
SEQ ID No. 12 is an amino acid sequence of a modified α-MSH[D-Phe]$_{(4-9)}$.
SEQ ID No. 13 is an amino acid sequence of a modified α-MSH[D-Phe]$_{(4-9)}$.
SEQ ID No. 14 is an amino acid sequence of α-MSH$_{(4-11)}$.
SEQ ID No. 15 is an amino acid sequence of modified α-MSH$_{(4-11)}$.
SEQ ID No. 16 is an amino acid sequence of α-MSH[D-Phe]$_{(4-11)}$.
SEQ ID No. 17 is an amino acid sequence of a modified α-MSH[D-Phe]$_{(4-11)}$.
SEQ ID No. 18 is an amino acid sequence of α-MSH[D-Phe]$_{(4-11)}$.
SEQ ID No. 19 is an amino acid sequence of a modified α-MSH[D-Phe]$_{(4-11)}$.
SEQ ID No. 20 is an amino acid sequence of a modified α-MSH[D-Phe]$_{(4-11)}$.
SEQ ID No. 21 is an amino acid sequence of a modified α-MSH[D-Phe]$_{(4-11)}$.
SEQ ID No. 22 is an amino acid sequence of a modified α-MSH[D-Arg]$_{(4-11)}$.
SEQ ID No. 23 is an amino acid sequence of a modified α-MSH[D-Trp]$_{(4-11)}$.
SEQ ID No. 24 is an amino acid sequence of a modified α-MSH[D-Trp]$_{(4-11)}$.
SEQ ID No. 25 is an amino acid sequence of a linear analog of α-MSH$_{(1-13)}$.
SEQ ID No. 26 is an amino acid sequence of [D-Ser$^1$, D-Phe$^7$]-α-MSH$_{(1-13)}$.
SEQ ID No. 27 is an amino acid sequence of [D-Tyr$^2$, D-Phe$^7$]-α-MSH$_{(1-13)}$.
SEQ ID No. 28 is an amino acid sequence of [D-Ser$^a$, D-Phe$^7$]-α-MSH$_{(1-13)}$.
SEQ ID No. 29 is an amino acid sequence of [D-Met$^4$, D-Phe$^7$]-α-MSH$_{(1-13)}$.
SEQ ID No. 30 is an amino acid sequence of [D-Glu$^5$, D-Phe$^7$]-α-MSH$_{(1-13)}$.
SEQ ID No. 31 is an amino acid sequence of [D-His$^6$, D-Phe$^7$]-α-MSH$_{(1-13)}$.
SEQ ID No. 32 is an amino acid sequence of [D-Phe$^7$, D-Arg$^8$]-α-MSH$_{(1-13)}$.
SEQ ID No. 33 is an amino acid sequence of [D-Phe$^7$, D-Trp$^9$]-α-MSH$_{(1-13)}$.
SEQ ID No. 34 is an amino acid sequence of [D-Phe$^7$, D-Lys$^{11}$]-α-MSH$_{(1-13)}$.
SEQ ID No. 35 is an amino acid sequence of [D-Phe$^7$, D-Pro$^{12}$]-α-MSH$_{(1-13)}$.
SEQ ID No. 36 is an amino acid sequence of [D-Phe$^7$, D-Val$^{13}$]-α-MSH$_{(1-13)}$.
SEQ ID No. 37 is an amino acid sequence of [D-Ser$^1$, Nle$^4$, D-Phe$^7$]-α-MSH$_{(1-13)}$.
SEQ ID No. 38 is an amino acid sequence of [D-Tyr$^2$, Nle$^4$, D-Phe$^7$]α-MSH$_{(1-13)}$.
SEQ ID No. 39 is an amino acid sequence of [D-Ser$^1$, Nle$^4$, D-Phe$^7$]-α-MSH$_{(1-13)}$.
SEQ ID No. 40 is an amino acid sequence of [Nle$^4$, D-Glu$^5$, D-Phe$^7$]-α-MSH$_{(1-13)}$.
SEQ ID No. 41 is an amino acid sequence of [Nle$^4$, D-His$^6$, D-Phe$^7$]-α-MSH$_{(1-13)}$.
SEQ ID No. 42 is an amino acid sequence of [Nle$^4$, D-Phe$^7$, D-Arg$^8$]-α-MSH$_{(1-13)}$.
SEQ ID No. 43 is an amino acid sequence of [Nle$^4$, D-Phe$^7$, D-Trp$^9$]-α-MSH$_{(1-13)}$.
SEQ ID No. 44 is an amino acid sequence of [Nle$^4$, D-Phe$^7$, D-Lys$^{11}$]-α-MSH$_{(1-13)}$.
SEQ ID No. 45 is an amino acid sequence of [Nle$^4$, D-Phe$^7$, D-Pro$^{12}$]-α-MSH$_{(1-13)}$.
SEQ ID No. 36 is an amino acid sequence of [Nle$^4$, D-Phe$^7$, D-Val$^{13}$]-α-MSH$_{(1-13)}$.
SEQ ID No. 47 is an amino acid sequence of a linear analog of α-MSH.
SEQ ID No. 48 is an amino acid sequence of a linear analog of α-MSH.
SEQ ID No. 49 is an amino acid sequence of a linear analog of α-MSH.
SEQ ID No. 50 is an amino acid sequence of a linear analog of α-MSH.
SEQ ID No. 51 is an amino acid sequence of a linear analog of α-MSH.
SEQ ID No. 52 is an amino acid sequence of a linear analog of α-MSH.
SEQ ID No. 53 is an amino acid sequence of a linear analog of α-MSH.
SEQ ID No. 54 is an amino acid sequence of a linear analog of α-MSH.
SEQ ID No. 55 is an amino acid sequence of a linear analog of α-MSH.
SEQ ID No. 56 is an amino acid sequence of a linear analog of α-MSH.
SEQ ID No. 57 is an amino acid sequence of a linear analog of α-MSH.
SEQ ID No. 58 is an amino acid sequence of a linear analog of α-MSH.
SEQ ID No. 59 is an amino acid sequence of a linear analog of α-MSH.
SEQ ID No. 60 is an amino acid sequence of a cyclo-[Cys$^4$-Cys$^{10}$]-α-MSH$_{(1-13)}$ analog.
SEQ ID No. 62 is an amino acid sequence of a Ac-cyclo-[Cys$^4$-Cys$^{10}$]-α-MSH$_{(4-13)}$ analog.
SEQ ID No. 61 is an amino acid sequence of a cyclo-[Cys$^4$-Cys$^{11}$]-α-MSH$_{(1-13)}$.
SEQ ID No. 63 is an amino acid sequence of a Ac-cyclo-[Cys$^4$-Cys$^{11}$]-α-MSH$_{(4-13)}$.
SEQ ID No. 64 is an amino acid sequence of a cyclo-[Cys$^5$-Cys$^{10}$]-α-MSH$_{(1-13)}$.

SEQ ID No. 65 is an amino acid sequence of a Ac-cyclo-[Cys$^5$-Cys$^{10}$]-α-MSH$_{(5-13)}$.

SEQ ID No. 66 is an amino acid sequence of a cyclo-[Cys$^5$-Cys$^{11}$]-α-MSH$_{(1-13)}$.

SEQ ID No. 67 is an amino acid sequence of a Ac-cyclo-[Cys$^5$-Cys$^{11}$]-α-MSH$_{(5-13)}$.

SEQ ID No. 68 is an amino acid sequence of a cyclo-[Cys$^4$-Cys$^{10}$][Cys$^5$-Cys$^{11}$]-α-MSH$_{(1-13)}$.

SEQ ID No. 69 is an amino acid sequence of a Ac-cyclo-[Cys$^4$-Cys$^{10}$][Cys$^5$-Cys$^{11}$]-α-MSH$_{(4-13)}$.

SEQ ID No. 70 is an amino acid sequence of a cyclo-[Cys$^4$-Cys$^{11}$][Cys$^5$-Cys$^{10}$]-α-MSH$_{(1-13)}$.

SEQ ID No. 71 is an amino acid sequence of a Ac-cyclo-[Cys$^4$-Cys$^{11}$][Cys$^5$-Cys$^{10}$]-α-MSH$_{(4-13)}$.

SEQ ID No. 72 is an amino acid sequence of a cyclo-[Cys$^4$-carba-Cys$^{10}$]-α-MSH$_{(1-13)}$.

SEQ ID No. 73 is an amino acid sequence of a cyclo-[Cys$^4$-carba-Cys$^{11}$]-α-MSH$_{(1-13)}$.

SEQ ID No. 74 is an amino acid sequence of a cyclo-[Cys$^5$-carba-Cys$^{10}$]-α-MSH$_{(1-13)}$.

SEQ ID No. 75 is an amino acid sequence of a cyclo-[Cys$^5$-carba-Cys$^{11}$]-α-MSH$_{(1-13)}$.

SEQ ID No. 76 is an amino acid sequence of a cyclo-[carba-Cys$^4$-Cys$^{10}$]-α-MSH$_{(1-13)}$.

SEQ ID No. 77 is an amino acid sequence of a cyclo-[carba-Cys$^5$-Cys$^{10}$]-α-MSH$_{(1-13)}$.

SEQ ID No. 78 is an amino acid sequence of a cyclo-[carba-Cys$^4$-Cys$^{11}$]-α-MSH$_{(1-13)}$.

SEQ ID No. 79 is an amino acid sequence of a cyclo-[carba-Cys$^5$-Cys$^{10}$]-α-MSH$_{(1-13)}$.

SEQ ID No. 80 is an amino acid sequence of a cyclo-[carba-Cys$^4$-carba-Cys$^{10}$]-α-MSH$_{(1-13)}$.

SEQ ID No. 81 is an amino acid sequence of a cyclo-[carba-Cys$^4$-carba-Cys$^{10}$]-α-MSH$_{(1-13)}$.

SEQ ID No. 82 is an amino acid sequence of a cyclo-[carba-Cys$^5$-carba-Cys$^{10}$]-α-MSH$_{(1-13)}$.

SEQ ID No. 83 is an amino acid sequence of a cyclo-[carba-Cys$^5$-carba-Cys$^{10}$]-α-MSH(Cys-Glu-His-D-Phe-Arg-Trp-Cys).

SEQ ID No. 84 is an amino acid sequence of a cyclo-[carba-Cys$^4$-carba-Cys$^{10}$][carba-Cys$^5$-carba-Cys$^{11}$]-α-MSH$_{(1-13)}$.

SEQ ID No. 85 is an amino acid sequence of a cyclo-[carba-Cys$^4$-carba-Cys$^{11}$][carba-Cys$^5$-carba-Cys$^{10}$]-α-MSH$_{(1-13)}$.

SEQ ID No. 86 is an amino acid sequence of a cyclo-[Cys$^4$-D-Lys$^8$, Cys$^{10}$]-α-MSH$_{(4-10)}$-OH.

SEQ ID No. 87 is an amino acid sequence of cyclo-[Cys$^4$-D-Lys$^8$, Phe$^9$, Cys$^{10}$]-α-MSH$_{(4-10)}$-OH.

SEQ ID No. 88 is an amino acid sequence of cyclo-[Cys$^4$-D-Arg$^8$, D-Cys$^{10}$]-α-MSH$_{(4-10)}$-OH.

SEQ ID No. 89 is an amino acid sequence of cyclo-[Cys$^4$-D-Lys$^8$, Phe$^9$, D-Cys$^{10}$]-α-MSH$_{(4-10)}$-OH.

SEQ ID No. 90 is an amino acid sequence of cyclo-[Cys$^4$-D-Lys$^8$, Trp$^9$, D-Cys$^{10}$]-α-MSH$_{(4-10)}$-OH.

SEQ ID No. 91 is an amino acid sequence of a α-MSH cyclic analog.

SEQ ID No. 92 is an amino acid sequence of a α-MSH cyclic analog.

SEQ ID No. 93 is an amino acid sequence of a α-MSH cyclic analog.

SEQ ID No. 94 is an amino acid sequence of a α-MSH cyclic analog.

SEQ ID No. 95 is an amino acid sequence of a α-MSH cyclic analog.

SEQ ID No. 96 is an amino acid sequence of a α-MSH cyclic analog.

SEQ ID No. 97 is an amino acid sequence of a α-MSH cyclic analog.

SEQ ID No. 98 is an amino acid sequence of a α-MSH$_{(1-12)}$-NH$_2$.

SEQ ID No. 99 is an amino acid sequence of a α-MSH$_{(1-11)}$-NH$_2$.

SEQ ID No. 100 is an amino acid sequence of a α-MSH$_{(4-13)}$-NH$_2$.

SEQ ID No. 101 is an amino acid sequence of Ac-cyclo (Cys$^4$-Cys$^{10}$)-α-MSH$_{(1-13)}$-NH$_2$.

SEQ ID No. 102 is an amino acid sequence of Ac-cyclo (Cys$^4$-D-Phe$^7$-Cys$^{10}$)-α-MSH$_{(4-13)}$-NH$_2$.

SEQ ID No. 103 is an amino acid sequence of Ac-cyclo (Cys$^4$,Cys$^{10}$)-α-MSH$_{(4-12)}$-NH$_2$.

SEQ ID No. 104 is an amino acid sequence of Ac-cyclo (Cys$^4$-D-Phe$^7$-Cys$^{10}$)-α-MSH$_{(4-12)}$-NH$_2$.

SEQ ID No. 105 is an amino acid sequence of Ac-cyclo (Cys$^4$,Cys$^{10}$)-α-MSH$_{(4-11)}$-NH$_2$.

SEQ ID No. 106 is an amino acid sequence of Ac-cyclo (Cys$^4$-D-Phe$^7$-Cys$^{10}$)-α-MSH$_{(4-11)}$-NH$_2$.

SEQ ID No. 107 is an amino acid sequence of Ac-cyclo (Cys$^4$,Cys$^{10}$)-α-MSH$_{(4-10)}$-NH$_2$.

SEQ ID No. 108 is an amino acid sequence of Ac-cyclo (Cys$^4$-D-Phe$^7$-Cys$^{10}$)-α-MSH$_{(4-10)}$-NH$_2$.

SEQ ID No. 109 is an amino acid sequence of Ac-cyclo (Cys$^4$-D-Phe$^7$-Cys$^{10}$)-α-MSH$_{(4-11)}$-NH$_2$.

SEQ ID No. 110 is an amino acid sequence of cyclo(Mpa$^4$, Cys$^{10}$)-α-MSH$_{(4-13)}$-NH$_2$.

SEQ ID No. 111 is an amino acid sequence of cyclo(Maa$^4$, Cys$^{10}$)-α-MSH$_{(4-13)}$-NH$_2$.

SEQ ID No. 112 is an amino acid sequence of Ac-cyclo (Hcy$^4$,Cys$^{10}$)-α-MSH$_{(4-13)}$-NH$_2$.

SEQ ID No. 113 is an amino acid sequence of Ac-Nle-cyclo(-Asp-His-D-Phe-Arg-Trp-Lys)-NH$_2$.

SEQ ID No. 114 is an amino acid sequence of Ac-Nle-cyclo(Asp-His-D-2'-Nal-Arg-Trp-Lys)-NH$_2$.

SEQ ID No. 115 is an amino acid sequence of Ac-Nle-cyclo(Asp-His-D-p-I-Arg-Trp-Lys)-NH$_2$.

SEQ ID No. 116 is an amino acid sequence of Ac-cyclo(-Asp-His-D-Phe-Arg-Trp-Lys)-N(CH$_3$)$_2$.

SEQ ID No. 117 is an amino acid sequence of Ac-cyclo(-Asp-His-D-Phe-Arg-Trp-Lys)-NH—CH$_2$—CH$_3$.

SEQ ID No. 118 is an amino acid sequence of Ac-cyclo(-Asp-Trp-D-Phe-Arg-Nal1-Lys)-NH—CH$_2$—CH$_3$.

SEQ ID No. 119 is an amino acid sequence of Ac-cyclo(-Asp-Trp-D-Phe-Arg-Nal1-Lys)-N(CH$_3$)$_2$.

SEQ ID No. 120 is an amino acid sequence of Ac-cyclo(-Asp-His-D-Phe-Arg-Nal1-Lys)-NH—CH$_2$—CH$_3$ (SEQ ID NO. 120).

SEQ ID No. 121 is an amino acid sequence of Ac-cyclo(-Asp-His-D-Phe-Arg-Nal1-Lys)-N(CH$_3$)$_2$ (SEQ ID NO. 121).

SEQ ID No. 122 is an amino acid sequence of Ac-Nle-cyclo(-Asp-His-D-Phe-Arg-Trp-Lys)-NH—CH$_2$—CH$_3$.

SEQ ID No. 123 is an amino acid sequence of Ac-Nle-cyclo(-Asp-His-Phe-Arg-Trp-Lys)-N(CH$_3$)$_2$.

SEQ ID No. 124 is an amino acid sequence of Ac-Nle-cyclo(-Asp-His-D-Phe-Arg-Nal1-Lys)NH—CH$_2$—CH$_3$.

SEQ ID No. 125 is an amino acid sequence of Ac-Nle-cyclo(-Asp-Trp-D-Phe-Arg-Nal1-Lys)NH—(CH$_3$)$_2$.

SEQ ID No. 126 is an amino acid sequence of Ac-Nle-cyclo(-Asp-His-D-Phe-Arg-Nal1-Lys)NH—CH$_2$—CH$_3$.

SEQ ID No. 127 is an amino acid sequence of Ac-Nle-cyclo(-Asp-Trp-D-Phe-Arg-Nal1-Lys)NH—CH$_2$—CH$_3$.

SEQ ID No. 128 is an amino acid sequence of α-MSH$_{(4-11)}$.

SEQ ID No. 129 is an amino acid sequence of α-MSH$_{(5-11)}$

SEQ ID No. 130 is an amino acid sequence of α-MSH$_{(4-9)}$.

SEQ ID No. 131 is an amino acid sequence of α-MSH$_{(5-13)}$.

SEQ ID No. 132 is an amino acid sequence of α-MSH$_{(1-13)}$.

SEQ ID No. 133 is an amino acid sequence of a α-MSH$_{(4-10)}$ cyclic analog.

BRIEF DESCRIPTION OF THE DRAWINGS

FIG. 1 illustrates melanocortin receptor agonist level in the blood as a function of time in a rat model for melanocortin receptor agonist MT-II administered orally and sub-cutaneous (SC).

DETAILED DESCRIPTION

The embodiments disclosed herein relate to pharmaceutical compositions, methods of manufacturing and methods of administering pharmaceutical compositions comprising melanocortin receptor agonists of a specific MC-receptor or of a number of MC-receptors, e.g. MC1, MC3, MC4 or/and MC5 receptors.

The embodiments disclosed herein relate to pharmaceutical compositions and methods of administering pharmaceutical compositions comprising pharmacologically active agents for use in treatment melanocortin receptor mediated disorders. As used herein, the term "pharmacologically active agent" relates to a chemical compound which induces a physiological or pharmacological effect and includes therapeutically effective agents, prophylactic effective agents or cosmetically effective agents.

There has been a long time effort devoted to the treatment of sexual dysfunction, including both male and female sexual dysfunction. To date, sexual dysfunction in male is generally treated by administration of phosphodiesterase 5 inhibitors (e.g. Viagra®), which acts on the vascular system, dopa receptor agonist (e.g. Ixense®), testosterone, and other drugs. Melanocortic agonist peptides have been shown to have distinct effects on sexual functions in that they cause erection.

The embodiments disclosed herein relate to pharmaceutical compositions and methods of administering pharmaceutical compositions comprising pharmacologically active agents for use in treatment of male sexual dysfunction, such as erectile dysfunction and female sexual dysfunction. In preferred embodiments, the methods for the treatment or prevention of male or female sexual dysfunction comprise administering orally, to a subject in need of such treatment or prevention, a therapeutically effective amount of a pharmaceutical composition comprising an agonist of melanocortin receptor. As used herein the term "composition" as in pharmaceutical composition relates to a product comprising one or more pharmacologically active ingredients or agents and one more inert ingredients as well as any product which result, directly or indirectly, from the combination, complexation or aggregation of any of two of more ingredients or from the dissociation of one or more ingredients, or from any other type of reactions or interactions of one or more ingredients.

As used herein, the term "erectile dysfunction" relates to a disorder involving the failure of a male subject to achieve erection, ejaculation or both. Symptoms of erectile dysfunction include an inability to achieve or maintain an erection, ejaculatory failure, premature ejaculation, and/or inability to achieve an orgasm. An increase in erectile dysfunction is often associated with age and/or may be caused by a physical disease or as a side-effect of drug treatment.

As used herein, the term "female sexual dysfunction" relates to conditions such as a lack of sexual desire and related arousal disorders, inhibited orgasm, lubrication difficulties, hypoactive sexual desire disorder, sexual anhedonia, sexual arousal disorder, dyspareunia and/or vaginismus.

The embodiments disclosed herein relate to pharmaceutical compositions and methods of administering pharmaceutical compositions, particularly in patients for whom a low to moderate single agent dose is not effective, for use in the treatment of sexual dysfunction. In some embodiments, the pharmaceutical composition has two or more therapeutic agents. The pharmaceutical composition, in some embodiments, has substantially reduced incidence of side effects observed with the use of melanocortin receptor agonists. For example, the pharmaceutical composition has a substantially reduced incidence of high blood pressure, nausea, loss of appetite, yawning, stretching and/or other side effects. In other embodiments, the pharmaceutical composition has substantially reduced incidence of side effects observed with the use of phosphodiesterase-5 inhibitors, such as, flushing, upset stomach, stuffy nose, urinary tract infection, visual changes, increased sensitivity to light, and diarrhea. Accordingly, in some embodiments, the methods herein permit inducing a therapeutic effect with minimal adverse side effects with a pharmaceutical composition having two or more therapeutic agents, particularly in patients for whom a low to moderate single agent dose is not effective.

The presently disclosed embodiments provide pharmaceutical compositions and methods for the treatment or the prevention of obesity or diabetes in mammals. Some embodiments provide pharmaceutical compositions and methods for the treatment or the prevention of endothelial dysfunction in mammals.

In some embodiments, the pharmaceutical compositions and methods of administering pharmaceutical compositions have the advantage to be more efficiently absorbed through the intestinal mucosal barrier. In some embodiments, the pharmaceutical compositions and methods of administering the pharmaceutical compositions have the advantage to provide for a greater safety margin between the therapeutic effects of the composition and the onset of undesired side effects than other compositions comprising melanocortin receptor agonists.

Pharmaceutical Compositions and Route of Administration

In some embodiments, the mode of delivery of the pharmaceutical compositions comprising the pharmacologically active agents is by oral delivery. Oral delivery of pharmacologically active agents is convenient, easy and painless, resulting in greater patient compliance relative to other modes of delivery. However, biological, chemical and physical barriers such as varying pH in the gastrointestinal tract, powerful digestive enzymes, and active agent impermeable gastrointestinal membranes, can make oral delivery of some pharmacologically active agents and transport through the intestinal walls into the blood stream problematic.

The embodiments disclosed herein provide pharmaceutical compositions acceptable for oral administration. The pharmaceutical compositions, in some embodiments, comprise at least one melanocortin receptor agonist as a pharmacologically active agent or a pharmaceutically acceptable salt thereof, and optionally other therapeutic agents. In some embodiments, the pharmaceutical compositions comprise at least one melanocortin receptor agonist, at least one protease inhibitor, and at least one delivery agent or absorption enhancer. The terms "delivery agent" and "absorption enhancer" are used herein interchangeably. In some embodiments, the use of at least one protease inhibitor and an absorption enhancer in a single oral composition increases the bioavailability of melanocortin receptor agonists of the presently disclosed embodiments. The absorption enhancer can, in some embodiments, enhance the absorption of the active ingredients, such as the melanocortin receptor agonists through the gastrointestinal mucosal barrier.

In some embodiments, the pharmaceutical compositions comprise an effective dosage of melanocortin receptor agonists, as a pharmacologically active agent, with addition of protease inhibitors and agents useful for delivering the particular pharmacologically active agents. In other embodiments, the pharmaceutical compositions comprise an effective dosage of melanocortin receptor agonists and an effective dosage of at least one other pharmacologically active agent together with at least one delivery agent useful for delivering the particular pharmacologically active agents. In some embodiments, methods of delivering a pharmaceutical compositions comprising an effective dosage of melanocortin receptor agonists, as a pharmacologically active agent, with addition of agents useful for delivering the particular pharmacologically active agents are disclosed. Yet in other embodiments, methods of delivering a pharmaceutical compositions comprising an effective dosage of melanocortin receptor agonists and at least one other pharmacologically active agent together with delivery agent(s) useful for delivering the particular pharmacologically active agents are disclosed.

Protease Inhibitors

In some embodiments, the protease inhibitors present in the pharmaceutical compositions can protect the melanocortin receptors agonists and other proteins or peptides against protein or peptide degradation. In some embodiments, the protease inhibitors can facilitate the absorption of melanocortin receptor agonists and/or other active ingredients in the intestine of a subject.

In some embodiments, the protease inhibitor comprises a trypsin inhibitor such as, but not limited to, Lima bean trypsin inhibitor, Aprotinin, soy bean trypsin inhibitor (SBTI), or Ovomucoid. In other embodiments, the protease inhibitor is a Cysteine protease inhibitor such as, but not limited to, cystatin, type 1 cystatins (or stefins), cystatins of type 2, human cystatins C, D, S, SN, and SA, cystatin E/M, cystatin F, type 3 cystatins, or kininogens or combinations thereof.

In some embodiments, the protease inhibitor comprises a chymotrypsin inhibitor, such as but not limited to, BBI.

In some embodiments, the protease inhibitor comprises a Threonine protease inhibitor. In some embodiments, the Threonine protease inhibitors comprise, but are not limited to, Bortezomib, MLN-519, ER-807446, TMC-95 A or combinations thereof.

In some embodiments, the protease inhibitor comprises an Aspartic protease inhibitor, such as, but not limited to, α2-Macroglobulin, Pepstatin A, Aspartic protease inhibitor 11, Aspartic protease inhibitor 1, Aspartic protease inhibitor 2, Aspartic protease inhibitor 3, Aspartic protease inhibitor 4, Aspartic protease inhibitor 5, Aspartic protease inhibitor 6, Aspartic protease inhibitor 7, Aspartic protease inhibitor 8, Aspartic protease inhibitor 9, Pepsin inhibitor Dit33, Aspartyl protease inhibitor, or Protease A inhibitor 3 or combinations thereof.

In some embodiments, the protease inhibitor comprises a metalloprotease inhibitor such as, but not limited to, Angiotensin-1-converting enzyme inhibitory peptide, Antihemorragic factor BJ46a, Beta-casein, Proteinase inhibitor CeKI, Venom metalloproteinase inhibitor DM43, Carboxypeptidase A inhibitor, smpI, IMPI, Alkaline proteinase, inh, Latexin, Carboxypeptidase inhibitor, Antihemorragic factor HSF, Testican-3, SPOCK3, TIMP1, Metalloproteinase inhibitor 1, Metalloproteinase inhibitor 2, TIMP2, Metalloproteinase inhibitor 3, TIMP3, Metalloproteinase inhibitor 4, TIMP4, Putative metalloproteinase inhibitor tag-225, Tissue inhibitor of metalloprotease, WAP, kazal, immunoglobulin, or kunitz and NTR domain-containing protein 1 or combinations thereof.

In some embodiments, the protease inhibitor comprises a suicide inhibitor, a transition state inhibitor, or a chelating agent. In some embodiments, the protease inhibitor is for example, but not limited to, AEBSF-HCl, (epsilon)-aminocaproic acid, (alpha) 1-antichymotypsin, antipain, antithrombin III, a 1-antitrypsin (α1-proteinase inhibitor), APMSF-HCl (4-amidinophenyl-methane sulfonyl-fluoride), sprotinin, benzamidine-HCl,chymostatin, DFP (diisopropylfluorophosphate), leupeptin, PEFABLOC® SC (4-(2-Aminoethyl)-benzenesulfonyl fluoride hydrochloride), PMSF (phenylmethyl sulfonyl fluoride), TLCK (1-Chloro-3-tosylamido-7-amino-2-heptanone HCl), TPCK (1-Chloro-3-tosylamido-4-phenyl-2-butanone), pentamidine isethionate, pepstatin, guanidium, α2-macroglobulin, a chelating agent of zinc, or iodoacetate, zinc or combinations thereof.

In some embodiments, the protease inhibitor is a combination of different protease inhibitors such as, but not limited to, a trypsin inhibitor, chymotrypsin inhibitor, Threonine protease inhibitor, Aspartic protease inhibitor, metalloprotease inhibitor, suicide inhibitor, a transition state inhibitor, chelating agent or combinations thereof.

In some embodiments, the amount of a protease inhibitor utilized in methods and compositions of the presently disclosed embodiments is at least 0.1 mg/dosage unit, 0.2 mg/dosage unit, 0.3 mg/dosage unit, 0.4 mg/dosage unit, 0.6 mg/dosage unit, 0.7 mg/dosage unit, 0.8 mg/dosage unit, 0.9 mg/dosage unit, 1 mg/dosage unit, 1.5 mg/dosage unit, 2 mg/dosage unit, 2.5 mg/dosage unit, 3 mg/dosage unit, 5 mg/dosage unit, 7 mg/dosage unit, 10 mg/dosage unit, 12 mg/dosage unit, 15 mg/dosage unit, 20 mg/dosage unit, 30 mg/dosage unit, 50 mg/dosage unit, 70 mg/dosage unit, 100 mg/dosage unit or 200 mg/dosage unit.

In some embodiments embodiment, the amount of a protease inhibitor utilized in the methods and compositions of the presently disclosed embodiments is at least 1000 k.i.u. (kallikrein inactivator units)/dosage unit, 10 k.i.u./dosage unit, 12 k.i.u./dosage unit, 15 k.i.u./dosage unit, 20 k.i.u./dosage unit, 30 k.i.u./dosage unit, 40 k.i.u./dosage unit, 50 k.i.u./dosage unit, 70 k.i.u./dosage unit, 100 k.i.u./dosage unit, 150 k.i.u./dosage unit, 200 k.i.u./dosage unit, 300 k.i.u./dosage unit, 500 k.i.u./dosage unit, 700 k.i.u./dosage unit, 1500 k.i.u./dosage unit, 3000 k.i.u./dosage unit, 4000 k.i.u./dosage unit, 5000 k.i.u./dosage unit.

Absorption Enhancer

In some embodiments, the pharmaceutical compositions comprise a delivery agent or absorption enhancer that enhances absorption of the active ingredients (e.g. melanocortin receptors agonists) through an intestinal mucosal barrier. As used herein the term "enhancer" enhances absorption of the pharmacologically active agents, such as the melanocortin receptors agonists, through the intestinal mucosal barrier. In some embodiments, enhancers, when used together with omega-3 fatty acids and/or a protease inhibitor, enhance the ability of a protein or peptide to be absorbed in the intestine. As provided herein, enhancers, when used together with omega-3 fatty acids and a protease inhibitor, enhance the ability of melanocortin receptor agonists to be absorbed in the intestine.

In some embodiments, the enhancer is didecanoylphosphatidylcholine (DDPC). In one embodiment, the enhancer is a chelating agent such as ethylenediaminetetraacetic acid (EDTA) or egtazic acid EGTA. For example, EDTA can be sodium-EDTA. In some embodiments, the enhancer can be a NO donor. In some embodiments, the enhancer can be a bile acid, glycine-conjugated form of a bile acid, or an alkali metal salt. In some embodiments, absorption enhancement can be achieved through utilization of a combination of α-galactosidase and β-mannanase. In some embodiments, the enhancer can be a fatty acid such as sodium caprate. In some embodiments, the enhancer can be sodium glycocholate. In some embodiments, the enhancer can be sodium salicylate. In some embodiments, the enhancer can be n-dodecyl-β-D-maltopyranoside. In some embodiments, surfactants can serve as absorption enhancer. In some embodiments, the enhancer can be chitisan such as N,N,N-trimethyl chitosan chloride (TMC).

In some embodiments, NO donors of the present invention comprise 3-(2-Hydroxy-1-(1-methylethyl)-2-nitrosohydrazino)-1-propanamine, N-ethyl-2-(1-ethyl-hydroxy-2-nitrosohydrazino)-ethanamine, or S-Nitrosa-N-acetyipenicillamine.

In some embodiments, the bile acid can be cholic acid. In some embodiments, the bile acid can be chenodeoxycholic acid, taurocholic acid, taurochenodeoxycholic acid, glycocholic acid, glycochenocholic acid, 3 beta-monohydroxychloric acid, lithocholic acid, 5 beta-cholanic acid, 3,12-diol-7-one-5 beta-cholanic acid, 3 alpha-hydroxy-12-ketocholic acid, 3 beta-hydroxy-12-ketocholic acid, 12 alpha-3 beta-dihydrocholic, acid, ursodesoxycholic acid or combinations thereof.

In some embodiments, the enhancer can be a nonionic surfactant. In one embodiment, the enhancer is a nonionic polyoxyethylene ether surface active agent (e.g. one having an HLB value of 6 to 19, wherein the average number of polyoxyethylene units is 4 to 30). In some embodiments, the enhancer can be an anionic surface active agents. In some embodiments, the enhancer can be a cationic surface active agent. In other embodiments, the enhancer can be an ampholytic surface active agent. In some embodiments, zwitteruionic surfactants, such as acylcarnitines, can serve as absorption enhancers.

In some embodiments, the delivery agents can be N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC) and their monosodium and disodium salts, ethanol solvates of their sodium salts and the monohydrates of their sodium salts or any combinations thereof, N-(5-(chlorosalicyloyl))-8-aminocaprylic acid (5-CNAC), disodium salt of 5-CNAC and the monohydrate thereof or combinations thereof. In some embodiments, the absorption enhancer can be CNAC, SNAD, SNAC, a monosodium and/or disodium salts thereof, ethanol solvates of sodium salts thereof and the 1 β monohydrates of sodium salts thereof, derivatives thereof or any combinations thereof.

In some embodiments, the absorption enhancer can be 8-(N-2-hydroxy-4-methoxybenzoyl)-aminocaprylic acid (4-MOAC) and pharmaceutically acceptable salts thereof and/or amorphous and polymorphic forms of 4-MOAC. In another embodiment, the absorption enhancer can be N-(8-[2-hydroxy-5-chlorobenzoyl]-amino)octanoic acid (also known as 8-(N-2-hydroxy-5-chlorobenzoyl)aminocaprylic acid)) (5-CNAC) and pharmaceutically acceptable salts thereof and/or amorphous and polymorphic forms of 5-CNAC. In other embodiments, the absorption enhancer can be 4-[(2-hydroxy-4-chlorobenzoyl)amino]butanoate (also known as 4-[(4-chloro-2-hydroxy-benzoyl)amino]butanoic acid) (4-CNAB) and pharmaceutically acceptable salts thereof, including its monosodium salt and/or amorphous and polymorphic forms of 4-CNAB.

Preferably, the delivery agent, e.g. 5 CNAC, SNAD, and SNAC, are very water soluble and nearly fully, i.e. greater than 85%, or greater than 90%, absorbed by the gastro-intestinal tract. The delivery agents may be delivered (e.g. ingested) in a coarse form or a micronized form. For example, the delivery agents can have an average particle size of about 1 mm. In some embodiments, the delivery agents can have an average particle size of less than 1 mm, less than 500 μm, less than 50 μm, less than 20 μm, or less than 10 μm.

The pharmaceutical compositions, in some embodiments, contain a delivery effective amount of one or more of the delivery agents, i.e. an amount sufficient to deliver the active agent for the desired effect. Generally, the delivery agent is present in an amount of 2.5% to 99.4% by weight, more preferably 25% to 50% by weight.

In some embodiments, the ratio of the melanocortin receptor agonist to the delivery agent and the protease inhibitor is 1:100:5. For example, the ratio of melanocortin receptor agonist to SNAC to SBTI is 1:100:5.

In some embodiments, the pharmaceutical compositions comprise an effective amount of one or more of the absorption enhancers to deliver the pharmacologically active agents for the desired therapeutic effect. For example, the pharmaceutical compositions can comprise an amount of 2.5% to 99.4% by weight of an absorption enhancer, 2.5% to 10% by weight of an absorption enhancer, 8% to 15% by weight of a absorption enhancer, 10% to 20% by weight of an absorption enhancer, 15% to 30% by weight of an absorption enhancer, 20% to 40% by weight of an absorption enhancer, 30% to 50% by weight of an absorption enhancer, 40% to 60% by weight of an absorption enhancer, 50% to 70% by weight of an absorption enhancer, or for example, 70% to 99.4% by weight of an absorption enhancer. In some embodiments, the amount of an absorption enhancer can be determined for any particular carrier or biologically or chemically active agent by methods known to those skilled in the art.

In some embodiments, the amount of enhancer utilized in methods and compositions comprises at least 0.1 mg/dosage unit, 0.2 mg/dosage unit, 0.3 mg/dosage unit, 0.4 mg/dosage unit, 0.6 mg/dosage unit. In another embodiment, the amount is 0.8 mg/dosage unit, 1 mg/dosage unit, 1.5 mg/dosage unit, 2 mg/dosage unit, 2.5 mg/dosage unit, 3 mg/dosage unit, 5 mg/dosage unit, 7 mg/dosage unit, 10 mg/dosage unit. 12 mg/dosage unit, 15 mg/dosage unit, 20 mg/dosage unit, 30 mg/dosage unit, 50 mg/dosage unit, 70 mg/dosage unit, 100 mg/dosage unit. In some embodiments, the amount of enhancer is 0.1-1 mg/dosage unit, 0.2-1 mg/dosage unit, 0.3-1 mg/dosage unit, 0.5-1 mg/dosage unit, 0.1-2 mg/dosage unit, 0.2-2 mg/dosage unit, 0.3-2 mg/dosage unit, 0.5-2 mg/dosage unit, 1-2 mg/dosage unit, 1-10 mg/dosage unit, 2-10 mg/dosage unit, 3-10 mg/dosage unit. 5-10 mg/dosage unit, 1-20 mg/dosage unit, 2-20 mg/dosage unit, 3-20 mg/dosage unit, 5-20 mg/dosage unit, 10-20 mg/dosage unit, 10-100 mg/dosage unit, 20-100 mg/dosage unit, 30-100 mg/dosage unit, 50-100 mg/dosage unit, is 10-200 mg/dosage unit, 20-200 mg/dosage unit, 30-200 mg/dosage unit, 50-200 mg/dosage unit, or 100-200 mg/dosage unit.

In some embodiments, the enhancer can be didecanoylphosphatidylcholine (DDPC). In another embodiment, the enhancer can be a chelating agent such as ethylenediaminetetraacetic acid (EDTA) or egtazic acid EGTA. For example, EDTA can be sodium-EDTA. In some embodiments, the chelating agent can provide protection against peptide and protein degradation.

In some embodiments, the enhancer is NO donor. NO donors comprises, but are not limited to, 3-(2-Hydroxy-1-(1-methylethyl)-2-nitrosohydrazino)-1-propanamine, N-ethyl-2-(1-ethyl-hydroxy-2-nitrosohydrazino)-ethanamine, or S-Nitroso-N-acetylpenicillamine or combinations thereof.

In some embodiments, the delivery agent or absorption enhancer is a bile acid, glycine-conjugated form of a bile acid, or an alkali metal salt. In some embodiments the bile acid comprises, but is not limited to, cholic acid, chenodeoxycholic acid, taurocholic acid, taurochenodeoxycholic acid, glycocholic acid, glycochenocholic acid, 3 beta-monohydroxychloric acid, lithocholic acid, 5 beta-cholanic acid, 3,12-diol-7-one-5 beta-cholanic acid, 3 alpha-hydroxy-12-ketocholic acid, 3 beta-hydroxy-12-ketocholic acid, 12 alpha-3 beta-dihydrocholic acid, ursodesoxycholic acid or combinations thereof.

In some embodiments, absorption enhancement can be achieved through utilization of a combination of α-galactosidase and β-mannanase. In some embodiments, the enhancer is a fatty acid such as sodium caprate. In some embodiments, the enhancer is sodium glycocholate. In some embodiments, the enhancer is sodium salicylate. In some embodiments, the enhancer is n-dodecyl-β-D-maltopyranoside. In some embodiments, surfactants can serve as absorption enhancer. In some embodiments, the enhancer is chitisan such as N,N, N-trimethyl chitosan chloride (TMC).

In some embodiments, omega-3 fatty acid can be added to the pharmaceutical composition. The omega-3 fatty acid can provide protection against peptide degradation. Omega-3 fatty acid can be found in vegetable sources such as the seeds of chia, perilla, flax, walnuts, purslane, lingonberry, seabuckthorn, and hemp, acai palm. In some embodiments, the omega-3 fatty acid can be provided to the composition in the form of fish oil, canola oil, flaxseed oil, or in the form of any other omega-3 fatty acid-rich source known in the art. In other embodiments, the omega-3 fatty acid can be provided in the form of a synthetic omega-3 fatty acid. In some embodiments, the omega-3 fatty acid includes, but is not limited to, omega-3 polyunsaturated fatty acid, DHA, an omega-3, polyunsaturated, 22-carbon fatty acid also referred to as 4,7,10,13,16,19-docosahexaenoic acid, omega-3 fatty acid such as linolenic acid (9, 12, 15-octadecatrienoic acid), stearidonic acid (6,9,12,15-octadecatetraenoic acid), eicosatrienoic acid (ETA; 11,14,17-eicosatrienoic acid), eicsoatetraenoic acid (8,11,14,17-eicosatetraenoic acid), eicosapentaenoic acid (EPA; 5,8,11,14,17-eicosapentaenoic acid), eicosahexaenoic acid (also referred to as "EPA"; 5,7,9,11,14,17-eicosahexaenoic acid), docosapentaenoic acid (DPA; 7,10,13,16,19-docosapenatenoic acid)tetracosahexaenoic acid (6,9,12,15,18,21-tetracosahexaenoic acid), any other omega-3 fatty acid known in the art and combinations thereof. In some embodiments, the presence of omega-3 fatty acid can improve the solubility of pharmacologically active agents.

In some embodiments, the absorption enhancer can be a nonionic surfactant. In some embodiments, the enhancer is a nonionic polyoxyethylene ether surface active agent (e.g. one having an HLB value of 6 to 19, wherein the average number of polyoxyethylene units is 4 to 30). In other embodiments, the enhancer is an anionic surface active agents. In other embodiments, the enhancer can be a cationic surface active agent. In other embodiments, the enhancer can be an ampholytic surface active agent. In other embodiments, zwitteruionic surfactants such as acylcarnitines can serve as absorption enhancers.

In some embodiments, the absorption enhancer can be a peptide, an amino acid or can be derived from amino acids.

Coating

In some embodiments, the pharmaceutical compositions further comprise a coating. The coating can inhibit digestion of the composition in a subject's stomach. In some embodiments, the coating allows for the release of the active ingredients when pH moves towards alkaline range in a subject's stomach. In some embodiments, the coating can be a monolayer, whereas in other embodiments, the coating can be applied in multilayers. In one embodiment, the coating is a bioadhesive polymer that selectively binds the intestinal mucosa and thus enables drug release in the attachment site. In some embodiments, the coating is an enteric coating. A number of materials may be used as enteric coatings. For example, tablets may be coated with shellac, sugar, biodegradable polysaccharide, chitosan, aquateric aqueous, aquacoat ECD, azo polymer, cellulose acetate phthalate, cellulose acetate trimelliate, liydroxypropylmethyl cellulose phthalate, gelatin, poly vinyl acetate phthalate, hydrogel, pulsincap or combinations thereof. In other embodiments, Eudragit®, an acrylic polymer, is used as the enteric coating. In another embodiment, the coating is a gelatin coating. In another embodiment, microencapsulation is used to protect the active ingredients such as melanocortin peptides against breakage in the stomach. Methods for applying a gelatin coating and for microencapsulation are well known in the art.

In one embodiment, the coating is a film-coating. In another embodiment, the coating is ethylcellulose or a water-based dispersion of ethylcellulose, e.g. hydroxypropylmethylcelulose (HPMC) E15.

In some embodiments, the coating is a gastro-resistant coating, e.g. a polymer containing carboxylic acid groups as a functional moiety. In another embodiment, the coating is a monolithic matrix. In another embodiment, the coating is cellulose ether (e.g. hypromellose or HPMC).

Antiemetic Agents

In some embodiments, the pharmaceutical compositions as described herein further comprise antiemetic agents to counteract transient side effects associated with the administration of melanocortin receptor agonists and/or the phosphodiesterase (PDE) inhibitors. In some embodiments, the antiemetic agents are co-administered with the pharmaceutical compositions disclosed herein. In preferred embodiments, the antiemetic agents are administered in a single oral composition to reduce the side effects associated with the administration of melanocortin receptor agonists.

In some embodiments, the antiemetic agents include, but are not limited to, 5-HT3 receptor antagonists, dopamine antagonists, NK1 receptor antagonist, H1 histamine receptor antagonists or antihistamines, cannabinoids, benzodiazepines, anticholinergics, Trimethobenzamide, Ginger, Emetrol, Peppermint, Muscimol, Ajwain and combinations thereof.

Melanocortin Receptor Agonists

As used herein a melanocortin receptor agonist relates to any endogenous or synthesized protein, peptide, compound, homologs or analogs thereof, which can interact with a melanocortin receptor and initiate a pharmacological response. The pharmacological response includes, but is not limited to, adenyl cyclase expression, characteristic of the melanocortin receptor. Melanocortin receptor agonists are useful in the treatment, control or prevention of diseases, disorders or conditions responsive to the activation of one or more of the melanocortin receptors including, but not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immune modulation, rheumatoid arthritis, skin tanning, acne and other skin disorders, neuroprotective and cognitive and memory enhancement including the treatment of Alzheimer's disease.

In some embodiments, the pharmaceutical compositions to treat sexual dysfunction comprise a melanocortin receptor agonist of MC-3-R or MC-4-R. In some embodiments, the agonist is an agonist selective of MC-4-R. In other embodiments, the agonist is an agonist selective of MC-3-R. However, the agonist can be a non-selective MC-3-R and/or MC-4-R agonist.

In some embodiments, the melanocortin receptor agonist is selected form the group of alpha-Melanocyte stimulating hormone (α-MSH or α-melanotropin) peptides, metabolites of and fragments of α-MSH and their analogs and homologs.

One should appreciate that the "peptides" according to the presently disclosed embodiments can be (a) naturally-occurring, (b) produced by chemical synthesis, (c) produced by recombinant DNA technology, (d) produced by biochemical or enzymatic fragmentation of larger molecules, (e) produced by methods resulting from a combination of methods (a) through (d), or (f) produced by any other means for producing peptides. In some embodiments, during chemical synthesis, it is possible to introduce various amino acids which do not naturally occur along the chain, modify the N- or C-terminus, and the like, thereby providing for improved stability and formulation, resistance to protease degradation, and the like. As used herein, the term "peptide" includes any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" includes dimers or multimers of peptides.

Peptide homologs refer to amino acid sequences with an amino acid substitution at any location. In one embodiment, the substitution can be made by any of the naturally occurring amino acids or unnaturally occurring amino acids. In various embodiments, the substitution is made by Phe, Lys, Trp, Tyr, Phe(4-Cl), Orn, Nal 1, or Bip. Homologs of the peptide may also include those sequences where one amino acid with an aromatic ring has been substituted for another amino acid with a different aromatic ring. An example of this substitution would be replacing a Phe residue with a Trp residue. Homologs of the peptide may also include those sequences where an amino acid with a charged side chain is replaced by another amino acid with or without a charged side chain. Examples of this include, without limitation, replacing an Arg residue (positively charged side chain) with a Lys (positively charged side chain) or replacing a His (positively charged side chain) with a Phe (nonpolar side chain).

According to some embodiments, the α-MSH peptides can be linear or cyclic. In some embodiments, the α-MSH peptides contain one or more asymmetric centers and can thus be present in racemic mixtures, single enantiomers, diastereomeric mixtures and individual diastereomers. The pharmaceutical compositions disclosed herein are meant to comprehend all such isomeric forms of α-MSH or other active ingredients.

It will be understood that, as used herein, references to the active compounds of the pharmaceutical compositions are meant to also include the pharmaceutically acceptable salts. The term "pharmaceutically acceptable salts" as used herein refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the presently disclosed embodiments is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

In some embodiments, the α-MSH peptide is a tridecapeptide having the sequence: Ac-Ser-Tyr-Ser-Met-Glu-His-Phe-Arg-Trp-Gly-Lys-Pro-Val (or as conventional written α-MSH$_{(1-13)}$, SEQ ID No. 1). In some embodiments, the α-MSH peptide is a heptapeptide having the sequence: Met-Glu-His-Phe-Arg-Trp-Gly (or as conventional written α-MSH$_{(4-10)}$, SEQ ID No. 2). In some embodiments, the Met amino acid is replaced by an oxidatively stable amino acid, norleucine (Nle), which is an isotere for Met. In some embodiments, the α-MSH peptides comprising Nle have an increased biological active when compared to the α-MSH peptides comprising the Met amino acid or the native α-MSH In some embodiments, the L-Phe can be replaced with a D-Phe to further enhance the biological activity of the α-MSH. It has been shown that substitution of Phe with the enantiomer D-Phe results in an peptide analog having an improved and prolonged biological activity (see U.S. Pat. No. 5,674,839). In some embodiments, the L-Tyr in the α-MSH$_{(1-13)}$ peptide can be replaced by D-Tyr.

In the listing of compounds according to the presently disclosed embodiments, the amino acid residues have their conventional meaning Thus, "Nle" refers to norleucine; "Asp" refers to aspartic acid; "His" refers to histidine; "D-Phe" refers to D-phenylalanine; "Arg" refers to arginine; "Trp" refers to tryptophan; "Lys" refers to lysine; "Gly" refers to glycine; "Pro" refers to proline; "Tyr" refers to tyrosine, "Ser" refers to serine, and "Orn" refers to ornithine.

In other embodiments, α-MSH linear or cyclic peptides include the core α-MSH$_{(4-10)}$ sequence His-Phe-Arg-Trp (SEQ ID NO. 3), His-D-Phe-Arg-Trp (SEQ ID NO. 4) or homologs or analogs of either of the foregoing. In some embodiments, in order to increase the biological activity of the native α-MSH, cyclic peptides comprising the core α-MSH sequence are used. In some embodiments, the His residue of the core α-MSH sequence is replaced with a Glu residue and a Lys residue is added at the N carboxyl terminus of the α-MSH peptide sequence. In some embodiments, cyclization occurs between the Asp amino acid and the Lys amino acid.

In some embodiments, the α-MSH peptides are deaminated so as not to include an amino group (—NH2) at its carboxyl terminus. In some embodiments, the deaminated α-MSH peptides comprises an hydroxyl group (—OH) at its carboxyl terminus forming a free acid form of the peptide. In some embodiments, the amino-terminus of peptide is acetylated (Ac-α-MSH).

In some embodiments, the melanocortin receptor against is a metallopeptide wherein the α-MSH peptide backbone is conformationally fixed to a metal ion. The use of metallopeptides can have the advantage of creating a fixed scaffold with the side chains of the individual amino acids remaining flexible, in contrast to a flexible peptide having a high rotational degree of freedom. In some embodiments, the metal ion can be selected from the group of Re, Tc, Cu, Ni, and Zn.

In general, the α-MSH peptides may be synthesized by solid-phase synthesis or other synthetic methods and purified according to methods in the art. For example, the linear compounds may be synthesized by solid-phase synthesis and purified according, for example, to the basic methods described by Sawyer et al [see P.N.A.S. U.S.A. 77:5754 (1980); P.N.A.S. U.S.A. 79:1751 (1982); or J. Med. Chem. 25:1022 (1982)], and the specific methods described by Al-Obeidi et al [see J. Med. Chem. 32:174 (1989), and J. Med. Chem. 32:25555 (1989)]. In some embodiments, the cyclic peptides can be synthesized by solid phase peptide synthesis using p-methylbenzhydrylamine resin. In some embodiments, the resin is swelled in DCM (dichloromethane) for three hours, neutralized with 10% DIEA/DCM, (DIEA is N,N-diisopropylethylamine) and washed with DCM three times before use. In some embodiments, the amino-terminus of the peptide-resin is acetylated. The protected peptide can then be cleaved from the resin and all protective group can be removed by HF. In some embodiments, the deprotected peptides can be cyclized by oxidation of the Cys residues. In some embodiments, all the amino acids are of the L-configuration with the exception of phenylalanine which can be of the D-configuration. α-MSH analogs suitable for use in the methods and compositions of the present embodiments include those disclosed in U.S. Pat. Nos. 4,457,864, 4,485,039, 4,649,191, 4,866,038, 4,918,055, 5,049,547, 5,576,290, 5,674,839, 5,683,981, 5,714,576, 5,731,408, 6,051,555, the disclosure of each of which is incorporated herein by reference in its entirety.

Linear α-MSH Peptide

In some embodiments, the linear analogs have the genera formula:

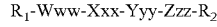

$R_1$-Www-Xxx-Yyy-Zzz-$R_2$ wherein $R_1$ is selected from the group of Ac-Gly, Ac-Met-Glu, Ac-Nle-Glu and Ac-Tyr-Glu wherein Www is selected from the group consisting of His and D-His, wherein Xxx is selected from the group consisting of Phe, D-Phe, Tyr, D-Tyr, (pNO₂)-D-Phe, wherein Yyy is selected from the group consisting of Arg and D-Arg, wherein Zzz is selected from the group consisting of Trp and D-Trp, and wherein is $R_2$ is selected from the group consisting of —NH₂, Gly-NH₂, Gly-Lys-NH₂.

In some embodiments, linear analogs of α-MSH$_{(4-10)}$ (SEQ ID NO. 2), α-MSH$_{(4-11)}$ (SEQ ID NO. 128), α-MSH$_{(5-11)}$ (SEQ ID NO. 129), α-MSH$_{(4-9)}$ (SEQ ID NO. 130), α-MSH$_{(5-13)}$ (SEQ ID No. 131) analog or α-MSH$_{(1-13)}$ (SEQ ID NO. 132), may be used.

In some embodiments, the analogs of α-MSH$_{(1-13)}$ may be selected form the group consisting of: Ac-Ser-Tyr-Ser-Met-Glu-His-Phe-Arg-Trp-Gly-Lys-Pro-Val-NH₂ (SEQ ID NO. 1), Ac-Ser-Tyr-Ser-Met-Glu-His-Phe-Arg-Trp-Gly-Lys-Pro-Val-OH (SEQ ID NO. 5), Ac-Ser-Tyr-Ser-Met-Glu-His-D-Phe-Arg-Trp-Gly-Lys-Pro-Val-NH₂ (or α-MSH[D-Phe⁷]$_{(1-13)}$, (SEQ ID NO. 6), Ac-Ser-Tyr-Ser-Met-Glu-His-D-Phe-Arg-Trp-Gly-Lys-Pro-Val-OH (SEQ ID NO. 7), Ac-Ser-Tyr-Ser-M-Glu-His-D-Phe-Arg-Trp-Gly-Lys-Pro-Val-NH₂ (SEQ ID NO. 8), wherein M is selected from the group of Met, Nle and Cys, acceptable pharmaceutical salts thereof or combinations thereof.

In some embodiments, the analogs of α-MSH$_{(4-10)}$ may be selected form the group consisting of Ac-Nle-Asp-His-D-Phe-Arg-Trp-Lys-NH₂ (SEQ ID NO. 9), Ac-Nle-Asp-His-D-Phe-Arg-Trp-Lys-OH (SEQ ID NO. 10), Ac-Met-Glu-His-Phe-Arg-Trp-Gly-NH₂ (or α-MSH$_{(4-10)}$, (SEQ ID NO. 11), acceptable pharmaceutical salts thereof or combinations thereof.

In some embodiments, the analogs of α-MSH$_{(4-9)}$ may be Ac-Nle-Asp-His-D-Phe-Arg-Trp-NH₂ (SEQ ID NO. 12), Ac-Nle-Asp-His-D-Phe-Arg-Lys-NH₂ (SEQ ID NO. 13), or acceptable pharmaceutical salts thereof.

In some embodiments, the analogs of α-MSH$_{(4-11)}$ may be selected form the group consisting of Ac-Met-Glu-His-Phe-Arg-Trp-Gly-Lys-NH₂ (SEQ ID NO. 14), Ac-Nle-Glu-His-Phe-Arg-Trp-Gly-Lys-NH₂ (SEQ ID NO. 15), Ac-Met-Glu-His-D-Phe-Arg-Trp-Gly-Lys-NH₂ (SEQ ID NO. 16), Ac-Nle-Glu-His-D-Phe-Arg-Trp-Gly-Lys-NH₂ (SEQ ID NO. 17), Ac-Met-Glu-His-(pNO₂)-D-Phe-Arg-Trp-Gly-Lys-NH₂ (SEQ ID NO. 18), Ac-Nle-Glu-His-D-Phe-Arg-Trp-Gly-Lys-NH₂ (SEQ ID NO. 19), Ac-Tyr-Glu-His-D-Phe-Arg-Trp-Gly-Lys-NH₂ (SEQ ID NO. 20), Ac-Nle-Glu-His-(pNO₂)-D-Phe-Arg-Trp-Gly-Lys-NH₂ (SEQ ID NO. 21), Ac-Nle-Glu-His-Phe-D-Arg-Trp-Gly-Lys-NH₂ (SEQ ID NO. 22), Ac-Nle-Glu-His-Phe-Arg-D-Trp-Gly-Lys-NH₂ (SEQ ID NO. 23), Ac-Nle-Glu-His-D-Phe-Arg-D-Trp-Gly-Lys-NH₂ (SEQ ID NO. 24), acceptable pharmaceutical salts thereof or combinations thereof.

In some embodiments, the linear analogs of α-MSH$_{(1-13)}$ have the general formula: Ac-Ser¹-Tyr²-Ser³-Yyy⁴-Glu⁵-His⁶-Xxx⁷-Arg⁸-Trp⁹-Gly¹⁰-Lys¹¹-Pro¹²-Val¹³-NH₂ ((SEQ ID NO. 25).

wherein Xxx⁷ and Yyy⁴ are amino residues, Xxx⁷ is in a D-isomeric configuration and all remaining amino acid residues are in an L-isomeric configuration. In some embodiments, Yyy⁴ is Met or Nle. In some embodiments Xxx⁷ is D-Phe. In some embodiments Xxx⁷ is D-Phe⁷ and Yyy⁴ is Nle. For example, the linear analogs of α-MSH$_{(1-13)}$ may be selected form the group consisting of: [D-Ser¹, D-Phe⁷]-α-MSH$_{(1-13)}$ (SEQ ID NO. 26), [D-Tyr², D-Phe⁷]-α-MSH$_{(1-13)}$ (SEQ ID NO. 27), [D-Ser³, D-Phe⁷]-α-MSH$_{(1-13)}$ (SEQ ID NO. 28), [D-Met⁴, D-Phe⁷]-α-MSH$_{(1-13)}$ (SEQ ID NO. 29), [D-Glu⁵, D-Phe⁷]-α-MSH$_{(1-13)}$ (SEQ ID NO. 30), [D-His⁶, D-Phe⁷]-α-MSH$_{(1-13)}$ (SEQ ID NO. 31), [D-Phe⁷, D-Arg⁸]-α-MSH$_{(1-13)}$ (SEQ ID NO. 32), [D-Phe⁷, D-Trp⁹]-α-MSH$_{(1-13)}$ (SEQ ID NO. 33), [D-Phe⁷, D-Lys¹¹]-α-MSH$_{(1-13)}$ (SEQ ID NO. 34), [D-Phe⁷, D-Pro¹²]-α-

MSH$_{(1-13)}$ (SEQ ID NO. 35), [D-Phe$^7$, D-Val$^{13}$]-α-MSH$_{(1-13)}$ (SEQ ID NO. 36), [D-Ser$^1$, Nle$^4$, D-Phe$^7$]-α-MSH$_{(1-13)}$ (SEQ ID NO. 37), [D-Tyr$^2$, Nle$^4$, D-Phe$^7$]-α-MSH$_{(1-13)}$ (SEQ ID NO. 38), [D-Ser$^1$, Nle$^4$, D-Phe$^7$]-α-MSH$_{(1-13)}$ (SEQ ID NO. 39), [Nle$^4$, D-Glu$^5$, D-Phe$^7$]-α-MSH$_{(1-13)}$ (SEQ ID NO. 40), [Nle$^4$, D-His$^6$, D-Phe$^7$]-α-MSH$_{(1-13)}$ (SEQ ID NO. 41), [Nle$^4$, D-Phe$^7$, D-Arg$^8$]-α-MSH$_{(1-13)}$ (SEQ ID NO. 42), [Nle$^4$, D-Phe$^7$, D-Trp$^9$]-α-MSH$_{(1-13)}$ (SEQ ID NO. 43), [Nle$^4$, D-Phe$^7$, D-Lys$^{11}$]-α-MSH$_{(1-13)}$ (SEQ ID NO. 44), [Nle$^4$, D-Phe$^7$, D-Pro$^{12}$]-α-MSH$_{(1-13)}$ (SEQ ID NO. 45), [Nle$^4$, D-Phe$^7$, D-Val$^{13}$]-α-MSH$_{(1-13)}$ (SEQ ID NO. 46), acceptable pharmaceutical salts thereof or combinations thereof.

In some embodiments, the linear analogs of α-MSH have the general formula:

Ac-Nle-Xxx-His-Zzz-Arg-Trp-Yyy-NH$_2$ (SEQ ID NO. 47)

wherein Xxx is either Glu or Asp, Zzz is Phe or D-Phe and Yyy is a dibasic amino acid such as lysine, ornithine, 2,4 diaminobutyric acid (Dbu) or 2,3 diamino propionic acid (Dpr).

For example, the linear analogs of α-MSH include, but are not limited to, Ac-Ser-Tyr-Ser-Nle-Glu-His-D-Phe-Arg-Trp-Lys-Gly-Pro-Val-NH$_2$ (SEQ ID NO. 48), Ac-Ser-Tyr-Ser-Nle-Asp-His-D-Phe-Arg-Trp-Lys-Gly-Pro-Val-NH$_2$ (SEQ ID NO. 49), Ac-Nle-Glu-His-D-Phe-Arg-Trp-Lys-Gly-Pro-Val-NH$_2$ (SEQ ID NO. 50), Ac-Nle-Asp-His-D-Phe-Arg-Trp-Gly-NH$_2$ (SEQ ID NO. 51), Ac-Nle-Asp-His-D-Phe-Arg-Trp-Lys-NH$_2$ (SEQ ID NO. 52), Ac-Nle-Asp-His-D-Phe-Arg-Trp-Orn-NH$_2$ (SEQ ID NO. 53), Ac-Nle-Glu-His-D-Phe-Arg-Trp-Orn-NH$_2$ (SEQ ID NO. 54), Ac-Nle-Glu-His-D-Phe-Arg-Trp-Dbu-NH$_2$ (SEQ ID NO. 55), Ac-Nle-Asp-His-D-Phe-Arg-Trp-Dbu-NH$_2$ (SEQ ID NO. 56), Ac-Nle-Asp-His-D-Phe-Arg-Trp-Dpr-NH$_2$ (SEQ ID NO. 57), Ac-Nle-Asp-His-D-Phe-Arg-Trp-Dbu-NH$_2$ (SEQ ID NO. 57), Ac-Nle-Glu-His-D-Phe-Arg-Trp-Dbu-NH$_2$ (SEQ ID NO. 58), acceptable pharmaceutical salts thereof or combinations thereof.

In some embodiments, the linear analogs of α-MSH can have the general formula AA$_1$-Nle-AA$_2$-His-AA$_3$-Arg-Trp-AA$_4$-AA$_5$ (SEQ ID NO. 59), wherein AA$_1$ is selected from the group of Ac-Ser, Tyr-Ser and Ac, wherein AA$_2$ is selected from the group of amino acid residues consisting of Glu and Asp wherein AA$_3$ is selected from the group of amino acid residues consisting of D-Phe and Phe, Arg, Trp, wherein AA$_4$ is selected from the group of amino acid residues consisting of Lys, Gly, Orn, Dbu, Dpr and wherein AA$_5$ is selected from the group of amino acid residues consisting of OH, NH$_2$, Gly-Val,-Pro-NH$_2$, and Gly-Val,-Pro-OH, wherein Dbu is 2,4 diaminobutyric acid and Dpr is 2,3 diaminopropionic acid.

In some embodiments, the linear analogs of α-MSH peptides are deaminated so as not to include an amino group (—NH$_2$) at its carboxyl terminus. In some embodiments, the deaminated α-MSH peptide comprises an hydroxyl group (—OH) at its carboxyl terminus forming a free acid form of the peptide.

Cyclic Analogs of α-MSH

In some embodiments, cyclic bridged analogs of α-MSH, α-MSH or fragment thereof may be used. In some embodiments, cyclic α-MSH analogs comprises at least one physiologically stable intramolecular interaction. In an exemplary embodiment, a physiologically stable intramolecular interaction can be formed between the amino residue at the number position 4 and the amino residue at the number position 10 or 11, and/or between the amino residue at the number position 5 and the amino residue at the number position 10 or 11. In some embodiments, the α-MSH analog is a cyclo-[Cys$^4$-Cys$^{10}$]-α-MSH$_{(1-13)}$ analog (SEQ ID NO. 60), or Ac-cyclo-[Cys$^4$-Cys$^{10}$]-α-MSH$_{(4-13)}$ (SEQ ID NO. 61), in which the intramolecular interaction is a covalent disulfide bond between one Cys residue being substituted for Met$^4$ and the other Cys residue being substituted for Gly$^{10}$. Cyclic analogs of α-MSH can be formed through covalent bonds other than disulfide bonds. In some embodiments, carba and dicarba α-MSH analogs may be used. In some embodiments, the cyclic analogs of α-MSH may be selected from the group consisting of: cyclo-[Cys$^4$-Cys$^{10}$]-α-MSH$_{(1-13)}$ (SEQ ID NO. 60), Ac-cyclo-[Cys$^4$-Cys$^{10}$]-α-MSH$_{(4-13)}$ (SEQ ID NO. 61), cyclo-[Cys$^4$-Cys$^{11}$]-α-MSH$_{(1-13)}$ (SEQ ID NO. 62), Ac-cyclo-[Cys$^4$-Cys$^{11}$]-α-MSH$_{(4-13)}$ (SEQ ID NO. 63), cyclo-[Cys$^5$-Cys$^{10}$]-α-MSH$_{(1-13)}$ (SEQ ID NO. 64), Ac-cyclo-[Cys$^5$-Cys$^{10}$]-α-MSH$_{(5-13)}$ (SEQ ID NO. 65), cyclo-[Cys$^5$-Cys$^{11}$]-α-MSH$_{(1-13)}$ (SEQ ID NO. 66), Ac-cyclo-[Cys$^5$-Cys$^{11}$]-α-MSH$_{(5-13)}$ (SEQ ID NO. 67), cyclo-[Cys$^4$-Cys$^{10}$][Cys$^5$-Cys$^{11}$]-α-MSH$_{(1-13)}$ (SEQ ID NO. 68), Ac-cyclo-[Cys$^4$-Cys$^{10}$][Cys$^5$-Cys$^{11}$]-α-MSH$_{(4-13)}$ (SEQ ID NO. 69), cyclo-[Cys$^4$-Cys$^{11}$][Cys$^5$-Cys$^{10}$]-α-MSH$_{(1-13)}$ (SEQ ID NO. 70), Ac-cyclo-[Cys$^4$-Cys$^{11}$][Cys$^5$-Cys$^{10}$]-α-MSH$_{(4-13)}$ (SEQ ID NO. 71), cyclo-[Cys$^4$-carba-Cys$^{10}$]-α-MSH$_{(1-13)}$ (SEQ ID NO. 72), cyclo-[Cys$^4$-carba-Cys$^{11}$]-α-MSH$_{(1-13)}$ (SEQ ID NO. 73), cyclo-[Cys$^5$-carba-Cys$^{10}$]-α-MSH$_{(1-13)}$ (SEQ ID NO. 74), cyclo-[Cys$^5$-carba-Cys$^{11}$]-α-MSH$_{(1-13)}$ (SEQ ID NO. 75), cyclo-[carba-Cys$^4$-Cys$^{10}$]-α-MSH$_{(1-13)}$ (SEQ ID NO. 76), cyclo-[carba-Cys$^5$-Cys$^{10}$]-α-MSH$_{(1-13)}$ (SEQ ID NO. 77), cyclo-[carba-Cys$^4$-Cys$^{11}$]-α-MSH$_{(1-13)}$ (SEQ ID NO. 78), cyclo-[carba-Cys$^5$-Cys$^{10}$]-α-MSH$_{(1-13)}$ (SEQ ID NO. 79), cyclo-[carba-Cys$^4$-carba-Cys$^{10}$]-α-MSH$_{(1-13)}$ (SEQ ID NO. 80), cyclo-[carba-Cys$^4$-carba-Cys$^{10}$]-α-MSH$_{(1-13)}$ (SEQ ID NO. 81), cyclo-[carba-Cys$^5$-carba-Cys$^{10}$]-α-MSH$_{(1-13)}$, (SEQ ID NO. 82), cyclo-[carba-Cys$^5$-carba-Cys$^{10}$]-α-MSH(Cys-Glu-His-D-Phe-Arg-Trp-Cys) (SEQ ID NO. 83), cyclo-[carba-Cys$^4$-carba-Cys$^{10}$][carba-Cys$^5$-carba-Cys$^{10}$]-α-MSH$_{(1-13)}$ (SEQ ID NO. 84), cyclo-[carba-Cys$^4$-carba-Cys$^{11}$][carba-Cys$^5$-carba-Cys$^{10}$]-α-MSH$_{(1-13)}$ (SEQ ID NO. 85), acceptable pharmaceutical salts thereof or combinations thereof.

In some embodiments, the cyclic α-MSH analogs are selected from the group consisting of: cyclo-[Cys$^4$-D-Lys$^8$, Cys$^{10}$]-α-MSH$_{(4-10)}$-OH (SEQ ID NO. 86), cyclo-[Cys$^4$-D-Lys$^8$, Phe$^9$, Cys$^{10}$]-α-MSH$_{(4-10)}$-OH (SEQ ID NO. 87), cyclo-[Cys$^4$-D-Arg$^8$, D-Cys$^{10}$]-α-MSH$_{(4-10)}$-OH (SEQ ID NO. 88), cyclo-[Cys$^4$-D-Lys$^8$, Phe$^9$, D-Cys$^{10}$]-α-MSH$_{(4-10)}$-OH (SEQ ID NO. 89), cyclo-[Cys$^4$-D-Lys$^8$, Trp$^9$, D-Cys$^{10}$]-α-MSH$_{(4-10)}$-OH (SEQ ID NO. 90), acceptable pharmaceutical salts thereof or combinations thereof.

In some embodiments, the cyclic bridged analogs of α-MSH may be selected from the group consisting of: Ac-Nle-cyclo(Asp-His-D-Phe-Arg-Trp-Lys)-NH$_2$ (SEQ ID NO. 91), Ac-Nle-cyclo(Asp-His-D-Phe-Arg-Trp-Lys)-Gly-NH$_2$ (SEQ ID NO. 92), Ac-Nle-cyclo(Asp-His-D-Phe-Arg-Trp-Lys)-Gly-Pro-NH$_2$ (SEQ ID NO. 93), Ac-Ser-Tyr-Ser-Nle-cyclo(Asp-His-D-Phe-Arg-Trp-Lys)-NH$_2$ (SEQ ID NO. 94), Ac-Ser-Nle-cyclo(Asp-His-D-Phe-Arg-Trp-Lys)-NH$_2$ (SEQ ID NO. 95), Ac-Nle-cyclo(Asp-His-D-Phe-Arg-Trp-Lys)-OH (SEQ ID NO. 133), acceptable pharmaceutical salts thereof or combinations thereof.

In some embodiments, the cyclic bridged analogs of α-MSH may be selected from the group consisting of: Ac-Ser-Tyr-Ser-cyclo-(Cys-Glu-His-D-Phe-Arg-Trp-Cys)-Lys-Pro-Val-NH$_2$ (SEQ ID NO. 96), Ac-Nle-cyclo-(Asp-His-D-

Phe-Arg-Trp-Lys)-NH$_2$ (SEQ ID NO. 97), Ac-Nle-cyclo-(X-D-Phe-Y)—R1 or Ac-Nle-cyclo-(X-D-Phe-Z)—R2, wherein:
- (a) X may be either a L- or D-amino acid having an omega-amino or carboxyl group in the side chain and γ-diaminopropionic acid, αγ-diaminobutyric acid, Orn, Lys, α-aminoadipic acid, α-aminopimelic acid, or higher (i.e. alkyldionic acids containing more than 7 carbons) homologs, Glu or Asp;
- (b) wherein Y may be either a L- or D-amino acid having an ω-amino or carboxyl group in the side chain, for example, Y may be diaminopropionic acid, αγ-diaminobutyric acid, Orn, Lys, αβ-aminoadipic acid, α-aminopimelic acid, or higher homologs, Glu or Asp;
- (c) wherein R1 is the designation α-MSH$_{(1-13)}$-NH$_2$ (SEQ ID NO. 1), α-MSH$_{(1-12)}$-NH$_2$ (SEQ ID NO. 98), α-MSH$_{(1-11)}$-NH$_2$ (SEQ ID NO. 99), α-MSH$_{(4-13)}$-NH$_2$, (SEQ ID NO. 100), or α-MSH$_{(4-10)}$-NH$_2$ (SEQ ID NO. 2);
- (d) wherein Z may be a L- or D-amino acid having an omega-amino or carboxyl group in the side chain, for example, Z may be αβ-diaminopropionic acid, αγ-diaminobutyric acid, Orn, Lys, α-aminoadipic acid, α-aminopimelic acid, or higher homologs, Glu or Asp;
- (e) wherein R2 is the designation α-MSH$_{(1-13)}$-NH$_2$, (SEQ ID NO. 1), α-MSH$_{(1-12)}$-NH$_2$ (SEQ ID NO. 98), α-MSH$_{(1-11)}$-NH$_2$ (SEQ ID NO. 99), α-MSH$_{(4-13)}$-NH$_2$ (SEQ ID NO. 100), or α-MSH$_{(4-10)}$-NH$_2$ (SEQ ID NO. 2), and wherein the peptide may form a cyclic peptide through the use of a sequence Xxx of amino acids comprising at least one amino acid residues (for example 1, 2, 3, 4, or 5 amino acid residues), each of which may be of L- or D-configuration (such as, for example, Lys-Lys, Lys-Arg, Arg-Lys, Arg-Arg, Ser-Ser, or Nle-Nle) or a linear or branched spacer of, for example, the type NH$_2$—(CH$_2$)n-COOH, NH$_2$—(CH$_2$)$_n$—NH$_2$, or HOOC—(CH$_2$)$_n$—COOH wherein "n" may be an integer from 1 to 15.

In some embodiments, X is selected from the group of Glu and Asp; wherein X is Lys; wherein Y is Lys; wherein R1 is selected from the group of α-MSH$_{(1-13)}$ (SEQ ID NO. 1) and α-MSH$_{(4-10)}$ (SEQ ID NO. 2); wherein R2 is selected from the group of α-MSH$_{(1-13)}$ (SEQ ID NO. 1), α-MSH$_{(4-13)}$ (SEQ ID NO. 100), and α-MSH$_{(4-10)}$ (SEQ ID NO. 2); and wherein Xxx is selected from the group of Arg-Arg, Arg-Lys, Lys-Arg, Lys-Lys, Nle-Nle, Lys, D-Lys-D-Lys, Glu-Glu, Ser-Ser, and NH(CH$_2$)$_5$CO.

In some embodiments, the cyclic analogs of α-MSH are selected from the group consisting of: Ac-cyclo(Cys$^4$,Cys$^{10}$)-α-MSH$_{(1-13)}$-NH$_2$ (SEQ ID NO. 101), Ac-cyclo(Cys$^4$,Cys$^{10}$)-α-MSH$_{(4-13)}$-NH$_2$ (SEQ ID NO. 62), Ac-cyclo(Cys$^4$-D-Phe$^7$-Cys$^{10}$)-α-MSH$_{(4-13)}$-NH$_2$ (SEQ ID NO. 102), Ac-cyclo(Cys$^4$,Cys$^{10}$)-α-MSH$_{(4-12)}$-NH$_2$ (SEQ ID NO. 103), Ac-cyclo(Cys$^4$-D-Phe$^7$-Cys$^{10}$)-α-MSH$_{(4-12)}$-NH$_2$ (SEQ ID NO. 104), Ac-cyclo(Cys$^4$,Cys$^{10}$)-α-MSH$_{(4-10)}$-NH$_2$ (SEQ ID NO. 105), Ac-cyclo(Cys$^4$-D-Phe$^7$-Cys$^{10}$)-α-MSH$_{(4-11)}$-NH$_2$ (SEQ ID NO. 106), Ac-cyclo(Cys$^4$,Cys$^{10}$)-α-MSH$_{(4-10)}$-NH$_2$ (SEQ ID NO. 107), Ac-cyclo(Cys$^4$-D-Phe$^7$-Cys$^{10}$)-α-MSH$_{(4-10)}$-NH$_2$ (SEQ ID NO. 108), Ac-cyclo(Cys$^4$-D-Phe$^7$-Cys$^{10}$)-α-MSH$_{(4-10)}$-NH$_2$ (SEQ ID NO. 109), cyclo(Mpa$^4$, Cys$^{10}$)-α-MSH$_{(4-13)}$-NH$_2$ (SEQ ID NO. 110), cyclo(Maa$^4$,Cys$^{10}$)-α-MSH$_{(4-13)}$-NH$_2$ (SEQ ID NO. 111), Ac-cyclo(Hcy$^4$,Cys$^{10}$)-α-MSH$_{(4-13)}$-NH$_2$ (SEQ ID NO. 112), acceptable pharmaceutical salts thereof and combinations thereof. Maa indicates 2-Mercaptoacetic acid, Mpa indicates 3-Mercaptopropionic acid; and Hcy indicates Homocystein.

In some embodiments the cyclic peptides of α-MSH are selected from the group of Ac-Nle-cyclo(-Asp-His-D-Phe-Arg-Trp-Lys)-NH$_2$ (SEQ ID NO. 113).

In some embodiments, the cyclic analog peptides of α-MSH and have D-2'-naphtalanine (D-2'-Nal) or D-para-iodo-phenylalanine (D-p-I) at position 4 of the peptide. For example, the cyclic analog peptides can be selected from the group consisting of Ac-Nle-cyclo(Asp-His-D-2'-Nal-Arg-Trp-Lys)-NH$_2$ (SEQ ID NO. 114), Ac-Nle-cyclo(Asp-His-D-p-I-Arg-Trp-Lys)-NH$_2$ (SEQ ID NO. 115) or combinations thereof.

In some embodiments, the α-MSH cyclic peptides are deaminated so as not to include an amino group (—NH$_2$) at its carboxyl terminus. In some embodiments, the deaminated α-MSH peptide comprises an hydroxyl group (—OH) at its carboxyl terminus forming a free acid form of the peptide.

In some embodiments, the cyclic peptides include, but are not limited to, Ac-cyclo(-Asp-His-D-Phe-Arg-Trp-Lys)-N(CH$_3$)$_2$ (SEQ ID NO. 116), Ac-cyclo(-Asp-His-D-Phe-Arg-Trp-Lys)-NH—CH$_2$—CH$_3$ (SEQ ID NO. 117), Ac-cyclo(-Asp-Trp-D-Phe-Arg-Nal1-Lys)-NH—CH$_2$—CH$_3$ (SEQ ID NO. 118), Ac-cyclo(-Asp-Trp-D-Phe-Arg-Nal1-Lys)-N(CH$_3$)$_2$ (SEQ ID NO. 119), Ac-cyclo(-Asp-His-D-Phe-Arg-Nal1-Lys)-NH—CH$_2$—CH$_3$ (SEQ ID NO. 120), Ac-cyclo(-Asp-His-D-Phe-Arg-Nal1-Lys)-N(CH$_3$)$_2$ (SEQ ID NO. 121), and combinations thereof. In other embodiments, the cyclic peptides include, but are not limited to, Ac-Nle-cyclo(-Asp-His-D-Phe-Arg-Trp-Lys)-NH—CH$_2$—CH$_3$ (SEQ ID NO. 122), Ac-Nle-cyclo(-Asp-His-Phe-Arg-Trp-Lys)-N(CH$_3$)$_2$ (SEQ ID NO. 123), Ac-Nle-cyclo(-Asp-His-D-Phe-Arg-Nal1-Lys)NH—CH$_2$—CH$_3$ (SEQ ID NO. 124), Ac-Nle-cyclo(-Asp-Trp-D-Phe-Arg-Nal1-Lys)NH—(CH$_3$)$_2$ (SEQ ID NO. 125), Ac-Nle-cyclo(-Asp-His-D-Phe-Arg-Nal1-Lys)NH—CH$_2$—CH$_3$ (SEQ ID NO. 126), Ac-Nle-cyclo(-Asp-Trp-D-Phe-Arg-Nal1-Lys)NH—CH$_2$—CH$_3$ (SEQ ID NO. 127), acceptable pharmaceutical salts thereof and combinations thereof.

While certain presently disclosed embodiments are described primarily in the context of α-MSH, it is to be understood that other melanocortin receptor agonists may be employed. For example, the metallopeptide melanocortin receptor agonists disclosed in WO 02/064091; and WO 01/13112, U.S. Pat. No. 7,807,678 can be used. In some embodiments, the cyclic melanocortin receptor agonist is a C-terminus N-alkylated cyclic peptide as disclosed in U.S. Patent Application 2011/0009341. In some embodiments, melanocortin receptor-specific compounds disclosed in U.S. Pat. No. 5,714,576, U.S. Pat. No. 5,576,290, U.S. Pat. No. 5,674,839, U.S. Pat. No. 5,683,981, U.S. Pat. No. 6,794,489, U.S. Pat. No. 7,550,602, U.S. Pat. No. 7,473,760, U.S. Pat. No. 7,456,184, WO 03/006620, WO 04/005324, and U.S. 2005/0222014 can be used, which are incorporated herein in their entirety. In some embodiments, piperazine melanocortin receptor agonists are used (see U.S. Pat. No. 7,354,923). It is to be understood that the foregoing listing of patent applications disclosing melanocortin receptor agonists is intended to only be exemplary, and that other melanocortin receptor agonists, whether heretofore known or hereafter developed, may similarly be used in the practice of the presently disclosed embodiments.

It is to be understood that the listing of melanocortin receptor agonists is intended to only be exemplary, and that other melanocortin receptor agonists, whether heretofore known or hereafter developed, may similarly be used in the practice of the presently disclosed embodiments. The suitability of any particular melanocortin receptor agonist can be readily determined by evaluation of its potency and selectivity using literature methods followed by evaluation of its toxicity, absorption, metabolism, pharmacokinetics, etc. in accordance with standard pharmaceutical practice.

Other Active Agents

The embodiments disclosed herein relate to pharmaceutical compositions and methods of administering the pharmaceutical compositions comprising melanocortin receptor agonists and one or more active ingredients having a therapeutic effect. In some embodiments, the combination of two or more active pharmacologically agents can have a synergistic effect and thereby improves the effect obtained with each of the active agents on its own or the added effect of each active agent. In some embodiments, the synergistic effect refers to the ability of the combination of the presently disclosed embodiments to achieve an effect superior to the added effect of each active agent, or to the ability to use a dose level of each active agent at a dose level that is less than a therapeutic dose of either agent administered individually as a monotherapy. As used herein "active agent" or "therapeutic agent" are used interchangeably.

In some embodiments, the administration of a single pharmaceutical composition comprising two or more therapeutic agents produces the desired pharmacological response at a dose level of each agent that is less than a dose of either agent administered as monotherapy that produces the desired pharmacological response.

Treatment of Sexual Dysfunction

In some embodiments, the pharmaceutical composition for treatment of sexual dysfunction comprises at least one melanocortin receptor agonist and a second pharmaceutical agent such as a PDE-5 inhibitor, an alpha-adrenergic receptor antagonist, a sexual response related hormone, such as testosterone in males or estrogen in females, or any other compounds useful in treatment of sexual dysfunction.

In some embodiments, the pharmaceutical compositions further comprise Phosphodiesterase (PDE) inhibitors, such as type 3, type 4, type 5 and non-specific phosphodiesterase inhibitors. Non-specific phosphodiesterase inhibitors include, but are not limited to, theophylline, IBMX, pentoxifylline and papaverine, either alone or in combination with phentolamine, and direct vasodilators such as hydralazine, and combinations thereof. Examples of type 3 phosphodiesterase inhibitors that may be used include, but are not limited to, bipyridines such as milrinone and amirinone, imidazolones such as piroximone and enoximone, dihydropyridazinones such as imazodan, 5-methyl-imazodan, indolidan and IC11118233, quinolinone compounds such as cilostamide, cilostazol and vesnarinone, and other molecules such as bemoradan, anergrelide, siguazodan, trequinsin, pimobendan, SKF-94120, SKF-95654, lixazinone and isomazole and combinations thereof. Examples of suitable type 4 phosphodiesterase inhibitors include rolipram and rolipram derivatives such as RO20-1724, nitraquazone and nitraquazone derivatives such as CP-77059 and RS-25344-00, xanthine derivatives such as denbufylline and IC163197, and other compounds such as EMD54622, LAS-31025 and etazolate, and combinations thereof.

In some embodiments, the pharmaceutical compositions further comprise Phosphodiesterase-5 inhibitors (PDE-5 Inhibitors). Yet in other embodiments, the pharmaceutical compositions further comprise Phosphodiesterase-3 inhibitors (PDE-3 Inhibitors), Phosphodiesterase-4 inhibitors (PDE-4 Inhibitors), Phosphodiesterase-6 inhibitors (PDE-6 Inhibitors) or any combinations thereof.

Phosphodiesterase 5 inhibitors include, but are not limited to, 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), also known as 1-[[3-(6,7-dihydro-1-methyl-7-oxo-3-propyl-1R-pyrazolo[4,3-d]pyr-imidin-5-yl)-4-ethoxyphenyl]sulphonyl]-4-methylpiperazine (see EP-A-0463756 and U.S. Published Application No. 2003/0083228); (6R,12aR)-2,3,6,7,12,12a-hexahydro-2-methyl-6-(3,4-methylenedioxyl)-henyl)-pyrazino[2',1':6,1]pyrido[3,4-b]indole-1,4-dione (IC-351) (tadalafil), such as the compound of examples 1, 3, 7, 8, 78 and 95 of published international application WO 95/19978; [2-[2-ethoxy-5-(4-ethyl-piperazin-1-yl-1-sulphonyl)-phenyl]-5-methy-1-7-propyl-3H-imidazo[5,1-f][1,2,4]triazin-4-one (vardenafil), also known as 1-[[3-(3,4-dihydro-5-methyl-4-oxo-7-propyl-limidazo[5,1-f]-as-triazin-2-yl)-4-ethoxyphenyl]sulphonyl]-4-ethylpiperazine, (see WO 99/24433); 4-[(3-Chloro-4-methoxybenzyl)amino]-2-[2-(hydroxymethyl)-1-pyrrolidinyl]-N-(2-pyrimidinylmethyl)-5-pyrimidinecarboxamide (also known as avanafil) (see U.S. Pat. No. 6,797,709); 1-[4-ethoxy-3-(6,7-dihydro-1-methyl-7-oxo-3-propyl-1H-pyrazolo[4,3-d]pyrimidin-5-yl)phenyl-sulfonyl]-4-methylpiperazine (also known as sildenafil); bis-(2-{4-[4-ethoxy-3-(1-methyl-7-oxo-3-propyl-6,7-dihydro-1H-pyrazolo[4,3-d]pyrimidin-5-yl)-benzenesulfonyl]piperazin-1-yl}-ethyl)carbonate (also known as lodenafil); 5-Ethyl-3,5-dihydro-2-[5-([4-(2-hydroxyethyl)-1-piperazinyl]sulfonyl)-2-propoxyphenyl]-7-propyl-4H-pyrrolo[3,2-d]pyrimidin-4-one (also known as mirodenafil); 4-[2-Ethoxy-5-(4-ethylpiperazin-1-yl)sulfonyl-phenyl]-9-methyl-7-propyl-3,5,6,8-tetrazabicyclo[4.3.0]nona-3,7,9-trien-2-one (also known as vardenafil); 3-(1-methyl-7-oxo-3-propyl-4,7-dihydro-1H-pyrazolo[4,3-d]pyrimidin-5-yl)-N-[2-(1-methylpyrrolidin-2-yl)ethyl]-4-propoxybenzenesulfonamide (also known as udenafil); 5-(2-ethoxy-5-morpholinoacetylphenyl)-1-methyl-3-n-propyl-1,6-dihyd-ro-7H-pyrazolo[4,3-d]pyrimidin-7-one (see EP-A-0526004);

3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO 98/49166);

3-ethyl-5-[5-(4-ethylpiperazin-1-ylsulphonyl)-2-(2-methoxyethoxyl)pyridin-3-yl]-2-(pyridin-2-yl)methyl-2,6-dihydro-7H-pyrazolo[4,3-d]pyrimidin-7-one (see WO 99/54333);

(+)-3-ethyl-5-[5-(4-ethylpiperazin-1-ylsulphonyl)-2-(2-methoxy-1-(R-)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-(-[(1R)-2-methoxy-1-methylethyl]oxy)pyridin-3-yl}-2-methyl-2,6-dihydro-7H-pyrazolo[4,3-d]pyrimidin-7-one (see WO 99/54333);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-p-yrazolo[4,3-d]pyrimidin-5-yl]-3-pyridylsulphonyl}4-ethylpiperazine (see WO 01/27113);

5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113);

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113;

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112);

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112);

4-bromo-5-(pyridylmethylamino)-6-[3-(4-chlorophenyl)-propoxy]-3(2H)-pyridazinone;
1-[4-[(1,3-benzodioxol-5-yl methyl)ainiono]-6-chloro-2-quinozolinyl-]-4-piperidine-carboxylic acid, monosodium salt;
(+)-cis-5,6a,7,9,9,9a-hexahydro-2-[4-(trifluoromethyl)-phenylmethyl-5-methyl-cyclopent-4,5]imidazo[2,1-b]purin-4(3H)one; furaziocillin;
cis-2-hexyl-5-methyl-3,4,5,6a,7,8,9,9a-octahydrocyclopent [4,5]-imidazo[2,1-b]purin-4-one; 3-acetyl-1-(2-chlorobenzyl)-2-propyl indole-6-carboxylate; 3-acetyl-1-(2-chlorobenzyl)-2-propylindole-6-carboxylate;
4-bromo-5-(3-pyridylmethylamino)-6-(3-(4-chlorophenyl) propoxy)-3-(2-H)pyridazinone; 1-methyl-5(5-morpholinoacetyl-2-n-propoxyphenyl)-3-n-propyl-1,6-dihydro-7H-pyrazolo(4,3-d)pyrimidin-7-one;
1-[4-[(1,3-benzodioxol-5-ylmethyl)amino]-6-chloro-2-quinazolinyl]-4-piperidinecarboxylic acid, monosodium salt;
Pharmaprojects No. 4516 (Glaxo Wellcome);
Pharmaprojects No. 5051 (Bayer);
Pharmaprojects No. 5064 (Kyowa Hakko; see WO 96/26940);
Pharmaprojects No. 5069 (Schering Plough);
GF-196960 (Glaxo Wellcome);
E-8010 and E-4010 (Eisai);
Bay-38-3045 & 38-9456 (Bayer);
Sch-51866;
pyrazolo[4,3d]pyrimidin-7-ones disclosed in EP-A-0463756;
pyrazolo[4,3-d]pyrimidin-7-ones disclosed in EP-A-0526004;
pyrazolo[4,3d]pyrimidin-7-ones disclosed in published international patent application WO 93/06104;
isomeric pyrazolo[3,4]pyrimidin-4-ones disclosed in published international patent application WO 93/07149;
quinazolin-4-ones disclosed in published international patent application WO 93/12095; pyrido[3,2-d]pyrimdin-4-ones disclose in published international patent application WO 94/05661;
purin-6-ones (see WO 94/00453);
pyrazolo[4,3-d]pyrimidin-7-ones (see WO 98/49166);
pyrazolo[4,3-d]pyrimidehn-7-ones (see WO 99/54333);
pyrazolo[4,3-d]pyrimidin-4-ones (see EP-A-0995751);
pyrazolo[4,3-d]pyrimidin-7-ones (see WO 00/24745);
pyrazolo[4,3-d]pyrimidin-4-ones (see EP-A-0995750;
the compounds disclosed in published international application WO 95/19978;
the compounds disclosed in published international application WO 99/24433
the compounds disclosed in published international application WO 93/07124.
the compound WO 93/07124; or
compounds from Rotella D P, J. Med. Chem. 43:1257 (2000).

Examples of type 5 phospodiesterase inhibitors include zaprinast, MY5445, dipyridamole, vardenafil, avanafil, lodenafil, microdenafil, tadalafil, udenafil and sildenafil. Other suitable type 5 phosphodiesterase inhibitors are disclosed in PCT Publication Nos. WO 94/28902 and WO 96/16644.

It is to be understood that the foregoing listing of PDE-5 inhibitors is intended to only be exemplary, and that other PDE-5 inhibitors, whether heretofore known or hereafter developed, may similarly be used in the practice of the presently disclosed embodiments. The suitability of any particular PDE-5 inhibitor can be readily determined by evaluation of its potency and selectivity using literature methods followed by evaluation of its toxicity, absorption, metabolism, pharmacokinetics, etc. in accordance with standard pharmaceutical practice.

It has been shown that sexual dysfunction in men may be due to abnormally low levels of the male hormone testosterone. In addition, testosterone propionate has been shown to increase or augment female libido. Accordingly, it may be beneficial to treat sexual dysfunction in men or women with sexual dysfunction pharmaceutical compositions comprising an effective amount of melanocortin receptor agonists and testosterone.

In some embodiments, pharmaceutical compositions to treat sexual dysfunction further comprises additional compounds useful for the treatment of sexual dysfunction. Examples of compounds for the treatment of sexual dysfunction are preferably selected from but not limited to the group consisting of a phosphodiesterase inhibitor (for example, avanafil, lodenafil, mirodenafil, sildenafil, tadalafil, vardenafil, udenafil, and the like); a cyclic-GMP-specific phosphodiesterase inhibitor; prostaglandins; apomorphin; oxytocin modulators; human chorionic gonadotropin (HCG); luteinizing hormone (LH); α-adrenergic antagonists; androgens; selective androgen receptor modulators (SARMs); selective estrogen receptor modulator (SERM), buproprion; vasoactive intestinal peptide (VIP); neutral endopeptidase inhibitors (NEP); and neuropeptide Y receptor antagonists (NPY), papaverine and combinations thereof. SERM compounds include, but are not limited to, flutamide, nilutamide, zanoterone and bicutamide.

In some embodiments, the estrogen agonist/antagonist is (−)-cis-6-phenyl-5-[-4-(2-pyrrolidin-1-yl-ethoxy)-phenyl]-5,6,7,8-tetrahydro-napththalene-2-ol (also known as lasofoxifene) or an optical or geometric isomer thereof; a pharmaceutically acceptable salt, N-oxide, ester, quaternary ammonium salt; or a prodrug thereof. For example, the estrogen agonist/antagonist can be in the form of a D-tartrate salt. In other embodiments, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In other embodiments, pharmaceutical compositions to treat sexual dysfunction can further comprise additional erectogenic compounds useful for the treatment of sexual dysfunction in male subjects. Examples of compounds for the treatment of sexual dysfunction are preferably selected from, but not limited to, the group consisting of include vasodilators or related compounds, including the nitrates, long and short acting alpha-adrenoceptor blockers, ergot alkaloids, anti-hypertensives and the prostaglandins. Useful nitrates and similarly acting compounds include nitro-glycerine, isosorbide dinitrate, erythrityl tetranitrate, amyl nitrate, sodium nitroprusside, molsidomine, linsidomine chlorydrate ("SIN-1"), S-nitroso-N-acetyl-d,l-penicillamine ("SNAP"), S-nitroso-N-cysteine, S-nitroso-N-glutathione ("SNO-GLU") and diazenium diolates ("NONOates"). Natural prostaglandins that can be used include $PGE_0$, $PGE_1$, $PGA_1$, $PGB_1$, $PGF_1$ alpha, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, PGE, $PGF_3$ alpha. Semi synthetic and synthetic prostaglandins such as carboprost tromethamine, dinoprost tromethamine, dinoprostone, lipoprost, gemeprost, metenoprost, sulprostone and tiaprost can also be used. A particularly useful prostaglandin is prostaglandin $E_1$ ($PGE_1$) or its synthetic version, alprostadil. Esters of the prostaglandins, such as the methyl and ethyl esters, can also be used. Suitable alpha-adrenoceptor blockers include phenoxybenzamine, dibenamine, doxazosin, terazosin, phentolamine, tolazoline, prazosin, trimazosin, alfuzosin, tamsulosin and indoramin. Ergot alkaloids include yohimbine hydrochloride, ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride.

Other erectogenic compounds that can be used with melanocortin receptors agonists and include, but are not limited to, nimodipine, pinacidil, cyclandelate, isoxsuprine, chloromazine, haloperidol, Rec15/2739 and trazodone, as well as anti-hypertensive agents including diazoxide, hydralazine and minoxidil and combinations thereof.

Treatment of Diabetes, Metabolic Syndrome and Obesity

The α-melanotropin (e.g. MT-II) molecule has demonstrated agonist activity at the human melanocortin receptors subtype 4 (hMC4R). In addition to its effect on male and female sexual function and libido, agonist activity at the hMC4R level by oral administration of compositions comprising MT-II may be used to affect feeding behavior and regulation, insulin resistance, energy homeostasis and weight control.

The embodiments disclosed herein relate to pharmaceutical compositions and methods of administering the pharmaceutical compositions comprising melanocortin receptor agonists for the treatment of diabetes, metabolic syndrome, and/or obesity.

In some embodiments, pharmaceutical compositions and methods of administering the pharmaceutical compositions comprising melanocortin receptor agonists and one or more active ingredients having a therapeutic effect for the treatment of diabetes, metabolic syndrome and/or obesity are disclosed. In some embodiments, the pharmaceutical composition comprises at least one melanocortin receptor agonist and a second pharmaceutical agent useful in the treatment of diabetes, metabolic syndrome and/or obesity. Pharmaceutical agents useful in the treatment of diabetes, metabolic syndrome and/or obesity include, but are not limited to leptin, Neuropeptide Y (NPY) and Agouti-related peptide (AgRP) antagonists, or any other compounds having a role in regulating energy intake, appetite, metabolism, energy expenditure or having a therapeutic effect on diabetes, metabolic syndrome and/or obesity.

In some embodiments, pharmaceuticals compositions disclosed herein can be used orally to regulate appetite and body weight, suppress food intake and/or increase energy expenditure. These physiological responses of pharmaceutical compositions comprising melanocortin receptor agonists alone or in combination with additional therapeutic agent, such as such as leptin, Neuropeptide Y (NPY) and Agouti-related peptide (AgRP) antagonists, derivative therefrom or combinations therein, can be used as treatment options for diabetes, metabolic syndrome and obesity.

It is to be understood that the foregoing listing of pharmaceutical agent useful in the treatment of diabetes, metabolic syndrome and/or obesity is intended to only be exemplary, and that other pharmaceutical agent useful in the treatment of diabetes, metabolic syndrome and/or obesity, whether heretofore known or hereafter developed, may similarly be used in the practice of the presently disclosed embodiments. The suitability of any particular pharmaceutical agent useful in the treatment of diabetes, metabolic syndrome and/or obesity can be readily determined by evaluation of its potency and selectivity using literature methods followed by evaluation of its toxicity, absorption, metabolism, pharmacokinetics, etc. in accordance with standard pharmaceutical practice.

Formulations

In some embodiments, the method comprises administering orally to the subject a pharmaceutical composition comprising melanocortin receptor agonist. In some embodiments, the pharmaceutical compositions comprise an effective dosage of melanocortin receptor agonists as a pharmacologically active agent with addition of delivery agents useful for delivering the particular pharmacologically active agents and protease inhibitor or combination of protease inhibitors.

In some embodiments, the pharmaceutical compositions comprise an effective dosage of melanocortin receptor agonists as a pharmacologically active agent with addition of delivery agents useful for delivering the particular pharmacologically active agents and the addition of omega-3 fatty acid and/or the addition of EDTA (or a salt thereof).

In other embodiments, the pharmaceutical compositions comprise an effective dosage of melanocortin receptor agonists and an effective dosage of at least one other pharmacologically active agent together with at least one delivery agent useful for delivering the particular pharmacologically active agents and with the addition of omega-3 fatty acid and/or the addition of EDTA (or a salt thereof).

In some embodiments, the pharmaceutical compositions comprise a melanocortin receptor agonist and a delivery agent (e.g. SNAC or SNAD or derivatives thereof). In some embodiments, the pharmaceutical compositions comprise a melanocortin receptor agonist, a delivery agent (SNAC or SNAD or derivatives thereof), and an omega-3 fatty acid. In some embodiments, the pharmaceutical compositions comprise a melanocortin receptor agonist, a delivery agent (e.g. SNAC or SNAD or derivatives thereof), EDTA (or a salt thereof), and an omega-3 fatty acid.

In some embodiments, the method for treating sexual dysfunction in a human subject, comprises administering orally to the subject a pharmaceutical composition comprising melanocortin receptor agonist, phosphodiesterase 5 inhibitors, and a delivery agent (e.g. SNAC or SNAD or derivatives thereof). In some embodiments, the method for treating sexual dysfunction in a human subject comprises administering orally to the subject a pharmaceutical composition comprising melanocortin receptor agonist, phosphodiesterase 5 inhibitors, a delivery agent (e.g. SNAC or SNAD), and an omega-3 fatty acid. In some embodiments, the method for treating sexual dysfunction in a human subject comprises administering orally to the subject a pharmaceutical composition comprising melanocortin receptor agonist, phosphodiesterase 5 inhibitors, a delivery agent (e.g. SNAC or SNAD), EDTA (or a salt thereof), and an omega-3 fatty acid.

In some embodiments, the pharmaceutical compositions can further comprise at least one compound that induces erectile activity, for example, phosphodiesterase 5 inhibitor, testosterone, prostaglandin, luteinizing hormone, human chorionic gonadotropin and combinations thereof. In some embodiments, the pharmaceutical compositions can further comprise a compound selected form the group of selective androgen receptor modulator, selective estrogen receptor modulator or combinations thereof. For example, the selective androgen receptor modulator can be selected from the group of flutamide, nilutamide, zanoterone, bicalutamide, and combinations thereof. In some embodiments, the selective estrogen receptor modulator can be selected from the group of tamoxifen, 4-hydroxy tamoxifen, raloxifene, droloxifene, toremifene, centchroman, idoxifene, (−)-cis-6-phenyl-5-[-4-(2-pyrrolidin-1-yl-ethoxy)-phenyl]-5,6,7,8-tetrahy-dro-napththalene-2-ol, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof, pharmaceutically acceptable salts, N-oxides, esters, and quaternary ammonium salts thereof. In some embodiments, the phosphodiesterase 5 inhibitor can be selected from the group of avanafil, lodenafil, mirodenafil, tadalafil, vardenafil, udenafil, sildenafil citrate and pharmaceutical acceptable salts.

In some embodiments, the method comprises administering orally to the subject a pharmaceutical composition comprising melanocortin receptor agonist, a protease inhibitor or combination of protease inhibitors, and a delivery agent (e.g. SNAC or SNAD). In some embodiments, the method comprises administering orally to the subject a pharmaceutical composition comprising melanocortin receptor agonist, a protease inhibitor or combination of protease inhibitors, and a delivery agent (SNAC or SNAD), and an omega-3 fatty acid. In some embodiments, the method comprises administering orally to the subject a pharmaceutical composition comprising melanocortin receptor agonist, a protease inhibitor or combination of protease inhibitors and a delivery agent (e.g. SNAC or SNAD), EDTA (or a salt thereof), and an omega-3 fatty acid.

In other embodiments, the pharmaceutical compositions comprises at least one melanocortin receptor agonist, at least one protease inhibitor, and a carrier to deliver the active ingredients through a biological barrier. In some embodiments, the compositions comprise at least one pharmacologically active agent, a delivery agent (e.g. SNAC), a protease inhibitor, and EDTA or Na-EDTA. In another embodiment, the compositions comprise at least one pharmacologically active agent, a delivery agent (e.g. SNAC), a protease inhibitor, and an omega-3 fatty acid. In another embodiment, the compositions comprise at least one pharmacologically active agent, a delivery agent (e.g. SNAC), a protease inhibitor, EDTA or Na-EDTA, and an omega-3 fatty acid.

In some embodiments, the method for treating sexual dysfunction in a human subject, comprises administering orally to the subject a pharmaceutical composition comprising melanocortin receptor agonist, phosphodiesterase 5 inhibitors, a protease inhibitor, and a delivery agent (e.g. SNAC or SNAD). In some embodiments, the method for treating sexual dysfunction in a human subject comprises administering orally to the subject a pharmaceutical composition comprising melanocortin receptor agonist, phosphodiesterase 5 inhibitors, a protease inhibitor or combination of protease inhibitors, a delivery agent (e.g. SNAC or SNAD), and an omega-3 fatty acid. In some embodiments, the method for treating sexual dysfunction in a human subject comprises administering orally to the subject a pharmaceutical composition comprising melanocortin receptor agonist, phosphodiesterase 5 inhibitors, a protease inhibitor or combination of protease inhibitors, a delivery agent (e.g. SNAC or SNAD), EDTA (or a salt thereof), and an omega-3 fatty acid.

In some embodiments, the method for treating sexual dysfunction in a human subject comprises administering orally to the subject a pharmaceutical composition comprising melanocortin receptor agonist, phosphodiesterase 5 inhibitors, testosterone containing preparation, a protease inhibitor or combination of protease inhibitors, and a delivery agent (e.g. SNAC or SNAD). In some embodiments, the method for treating sexual dysfunction in a human subject comprises administering orally to the subject a pharmaceutical composition comprising melanocortin receptor agonist, phosphodiesterase 5 inhibitors, testosterone containing preparation, a protease inhibitor or combination of protease inhibitors, a delivery agent (e.g. SNAC or SNAD), and an omega-3 fatty acid. In some embodiments, the method for treating sexual dysfunction in a human subject comprises administering orally to the subject a pharmaceutical composition comprising melanocortin receptor agonist, phosphodiesterase 5 inhibitors, testosterone containing preparation, a protease inhibitor or combination of protease inhibitors, a delivery agent (e.g. SNAC or SNAD), EDTA (or a salt thereof), and an omega-3 fatty acid.

Yet in other embodiments, the method for treating sexual dysfunction in a human subject comprises administering orally to the subject a pharmaceutical composition comprising melanocortin receptor agonist, phosphodiesterase 5 inhibitors, testosterone containing preparation, and a delivery agent (e.g. SNAC or SNAD or derivatives thereof). In some embodiments, the method for treating sexual dysfunction in a human subject comprises administering orally to the subject a pharmaceutical composition comprising melanocortin receptor agonist, phosphodiesterase 5 inhibitors, testosterone containing preparation, a delivery agent (e.g. SNAC or SNAD), and an omega-3 fatty acid. In some embodiments, the method for treating sexual dysfunction in a human subject comprises administering orally to the subject a pharmaceutical composition comprising melanocortin receptor agonist, phosphodiesterase 5 inhibitors, testosterone containing preparation, a delivery agent (e.g. SNAC or SNAD), EDTA (or a salt thereof), and an omega-3 fatty acid.

In some embodiments, the method for treating sexual dysfunction in a human subject comprises administering orally to the subject a pharmaceutical composition comprising melanocortin receptor agonist, phosphodiesterase 5 inhibitors, testosterone containing preparation, selective androgen receptor modulator and/or selective estrogen receptor modulators, a protease inhibitor or combination of protease inhibitors, and a delivery agent (e.g. SNAC or SNAD). In some embodiments, the method for treating sexual dysfunction in a human subject comprises administering orally to the subject a pharmaceutical composition comprising melanocortin receptor agonist, phosphodiesterase 5 inhibitors, testosterone containing preparation, selective androgen receptor modulator and/or selective estrogen receptor modulators, a protease inhibitor or combination of protease inhibitors, a delivery agent (e.g. SNAC or SNAD), and an omega-3 fatty acid. In some embodiments, the method for treating sexual dysfunction in a human subject comprises administering orally to the subject a pharmaceutical composition comprising melanocortin receptor agonist, phosphodiesterase 5 inhibitors, testosterone containing preparation, selective androgen receptor modulator and/or selective estrogen receptor modulators, a protease inhibitor or combination of protease inhibitors, a delivery agent (e.g. SNAC or SNAD), EDTA (or a salt thereof), and an omega-3 fatty acid.

Yet in other embodiments, the method for treating sexual dysfunction in a human subject comprises administering orally to the subject a pharmaceutical composition comprising melanocortin receptor agonist, phosphodiesterase 5 inhibitors, testosterone containing preparation, selective androgen receptor modulator and/or selective estrogen receptor modulators, and a delivery agent (e.g. SNAC or SNAD). In some embodiments, the method for treating sexual dysfunction in a human subject comprises administering orally to the subject a pharmaceutical composition comprising melanocortin receptor agonist, phosphodiesterase 5 inhibitors, testosterone containing preparation, selective androgen receptor modulator and/or selective estrogen receptor modulators, a delivery agent (e.g. SNAC or SNAD), and an omega-3 fatty acid. In some embodiments, the method for treating sexual dysfunction in a human subject comprises administering orally to the subject a pharmaceutical composition comprising melanocortin receptor agonist, phosphodiesterase 5 inhibitors, testosterone containing preparation, selective androgen receptor modulator and/or selective estrogen receptor modulators, a delivery agent (e.g. SNAC or SNAD), EDTA (or a salt thereof), and an omega-3 fatty acid.

In some embodiments, the method for treating metabolic syndrome, diabetes and/or obesity in a human subject, comprises administering orally to the subject a pharmaceutical composition comprising melanocortin receptor agonist, a delivery agent (e.g. SNAC or SNAD or derivatives thereof), and a pharmaceutical agent useful in the treatment of metabolic syndrome, diabetes and/or obesity. In some embodiments, the method for treating metabolic syndrome, diabetes and/or obesity, comprises administering orally to the subject a pharmaceutical composition comprising melanocortin receptor agonist, a delivery agent (e.g. SNAC or SNAD or derivatives thereof), and a pharmaceutical agent useful in the treatment of metabolic syndrome, diabetes and/or obesity and a protease inhibitor.

In some embodiments, the method for treating metabolic syndrome, diabetes and/or obesity in a human subject comprises administering orally to the subject a pharmaceutical composition comprising melanocortin receptor agonist, leptin, a protease inhibitor or combination of protease inhibitors, a delivery agent (e.g. SNAC or SNAD), and an omega-3 fatty acid. Yet in other embodiments, the method for treating metabolic syndrome, diabetes and/or obesity in a human subject comprises administering orally to the subject a pharmaceutical composition comprising melanocortin receptor agonist, leptin, a delivery agent (e.g. SNAC or SNAD), and an omega-3 fatty acid.

In some embodiments, the method for metabolic syndrome, diabetes and/or obesity in a human subject comprises administering orally to the subject a pharmaceutical composition comprising melanocortin receptor agonist, leptin, a protease inhibitor or combination of protease inhibitors, a delivery agent (e.g. SNAC or SNAD), EDTA (or a salt thereof), and an omega-3 fatty acid. Yet in other embodiments, the method for metabolic syndrome, diabetes and/or obesity in a human subject comprises administering orally to the subject a pharmaceutical composition comprising melanocortin receptor agonist, leptin, a delivery agent (e.g. SNAC or SNAD), EDTA (or a salt thereof), and an omega-3 fatty acid.

In some embodiments, the pharmaceutical composition can further comprise pharmaceutical agents useful in the treatment of diabetes, metabolic syndrome and/or obesity. Pharmaceutical agents useful in the treatment of diabetes, metabolic syndrome and/or obesity include, but are not limited to leptin, Neuropeptide Y (NPY) and Agouti-related peptide (AgRP) antagonists, or any other compounds having a role in regulating energy intake, appetite, metabolism, energy expenditure or having a therapeutic effect on diabetes, metabolic syndrome and/or obesity.

Method of Preparation

In practical use, the active agents of the pharmaceutical composition can be combined in a homogeneous admixture with optionally inactive ingredients using conventional pharmaceutical compounding techniques known in the art. In preparing the compositions for oral dosage form, any of the usual pharmaceutical media may be employed. For example, in preparing oral liquid preparations, water, glycols, oils, alcohols, flavoring agents, preservatives, coloring agents and the like can be used. In preparing oral solid preparations such as, for example, powders, hard and soft capsules and tablets, carriers such as starches, sugars, gums, microcrystalline cellulose, diluents, granulating agents, lubricants, acrylate, calcium carbonate, magnesium oxide, talc, binders, disintegrating agents, fatty oil and the like and mixtures thereof, can be used.

In some embodiments, the binder includes, bus is not limited to, acacia, cornstarch, gelatin, carbomer, ethyl cellulose, guar gum, hydroxypropyl cellulose, hydroxypropyl methyl cellulose, povidone and combinations thereof. In some embodiments, the disintegrating agent includes, but is not limited to, cornstarch, potato starch, alginic acid, silicon dioxide, croscarmelose sodium, crospovidone, guar gum, sodium starch glycolate and combinations thereof.

In some embodiments, the buffers used to prepare the pharmaceutical composition are for example, Tris-HCL, acetate, phosphate, of various pH and ionic strength. In addition, additives such as albumin or gelatin to prevent absorption to surfaces, detergents (e.g., Tween 20, Tween 80, Pluronic F68, bile acid salts), surfactants (e.g. sodium lauryl sulfate), permeation enhancers, solubilizing agents (e.g., glycerol, polyethylene glycerol), anti-oxidants (e.g., ascorbic acid, sodium metabisulfite, butylatedhydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants may be added to the compositions.

In some embodiments, the dosage forms can be formulated to achieve an immediate release profile, an extended release profile, or a delayed release profile, as known to one skilled in the art.

In some embodiments, the melanocortin receptor agonist, the delivery agent (e.g. SNAC) and the at least one protease inhibitor are mixed with a caprylic acid buffer solution (pH 5.2). after mixing, pH is then raised and the mixture is lyophilized. The lyophilized powder is mixed with EDTA in a Teflon bottle at −20° C. for about 24 to 48 hours. Pills are then manufactured using 1 ton compression and coated with a polymer coating.

Analytical Assays

In some embodiments, following administration of the pharmaceutical composition described herein, the melanocortin receptor agonist is extracted from the plasma, serum or tissue and analyzed by HPLC followed by mass spectrometry (e.g. liquid chromatography/tandem mass spectrometry. (See Hatziieremia et al., Rapid Comm. Mass Spectrom., 2007, 21(15):2431-2438 and Mock S. et al., Rapid Comm. Mass Spectrom., 2002, 16:2142-2147). In some embodiments, the analyte can be extracted using solid phase extraction, ethanol precipitation, acetonitrile precipitation or combinations thereof. For quantitative assays, internal standards having similar extraction recovery and retention time and that do not interfere with the analytes can be added to the samples.

Clinical Applications

The embodiments disclosed herein relate to pharmaceutical compositions and methods of administering the pharmaceutical composition to a subject (specifically in mammals, and more specifically in, but not limited to, humans, male or female) to overcome sexual dysfunction, such as erectile dysfunction, and inhibited sexual desire syndrome. In some embodiments, the pharmaceutical composition can be used in treating impotency in elderly men whose testosterone levels may be declining with age. These individuals, although classified as organically dysfunctional, may respond to the pharmaceutical compositions of the presently disclosed embodiments in particular when the pharmaceutical composition comprises testosterone or other androgen compounds.

Other embodiments relate to pharmaceutical compositions and methods of administering the pharmaceutical composition to a subject (specifically in mammals, and more specifically in, but not limited to, humans) to achieve normalization of hypopigmentation dysfunctions such as post inflammatory hypopigmentation, including pityriasis, alba, tinea versicolor, vitiligo, idiopathic guttae hypomelanosis; and nevus depigmentosus. In some embodiments, the pharmaceutical compositions can achieve darkening of the skin in the total absence of sun or UV light irradiation.

Yet, other embodiments relate to pharmaceutical compositions and methods of administering the pharmaceutical composition to a subject (specifically in mammals, and more specifically in, but not limited to, humans) to achieve normalization of endothelial dysfunctions. Yet other embodiments relate to pharmaceutical compositions and methods of administering the pharmaceutical composition to a subject (specifically in mammals, and more specifically in, but not limited to, humans) to treat obesity. Yet other embodiments relate to pharmaceutical compositions and methods of administering the pharmaceutical composition to a subject (specifically in mammals, and more specifically in, but not limited to, humans) to treat metabolic syndrome, diabetes and/or obesity.

The compounds and methods disclosed herein can be used for both medical applications or veterinary applications. Typically, the methods are used in humans, but may also be used in other mammals. The term "subject" is intended to denote a mammalian individual, and is so used throughout the specification and in the claims.

It is to be understood that presently disclosed embodiments are capable of variations and modifications. Such alterations and changes may include, for example, different pharmaceutical compositions for the administration of the peptides according to the presently disclosed embodiments to a subject; different amounts of peptides in the compositions to be administered; different times and means of administering the peptides according to the presently disclosed embodiments; and different materials contained in the administration dose including, for example, combinations of different peptides, or combinations of erectogenic peptides with other biologically active (including but not limited to other erectogenic compounds) compounds. Such changes and alterations also are intended to include modifications in the amino acid sequence of the specific active peptides described herein (e.g. erectogenic peptide, Neuopeptide Y etc. . . . ) in which such changes alter the sequence in a manner as not to change the activity potential of the peptide (e.g. erectogenic potential etc. . . . ), but as to change solubility of the peptide in the pharmaceutical composition to be administered or in the body, absorption of the peptide by the body, protection of the peptide for either shelf life or within the body until such time as the biological action of the peptide is able to bring about the desired effect, and such similar modifications. Accordingly, such changes and alterations are properly intended to be within the full range of equivalents, and therefore within the purview of the following claims.

The contents of the above published patent applications, and in particular the general formulas and exemplified compounds therein, are incorporated in this specification in their entirety by reference thereto.

EXAMPLES

The example below is provided herein for illustrative purposes and is not intended to be restrictive.

Bioavailability of the oral preparation of α-Melanotropin (MT-II) was confirmed using the Sprague-Dawley (SD) rat model and is depicted in FIG. 1. The pharmaceutical kinetic data accumulated revealed that the drug is successfully delivered orally with the drug delivery system described herein. A greater than 30% bioavailability was achieved when compared to the positive control, defined as sub-cutaneous (SC) administration of α-Melanotropin (MT II) in preliminary studies. The SC study and oral administration study were performed on the same group of rats. In addition, a second successful study conducted on a different group of rats was performed to confirm the initial oral bioavailability results.

Materials and Methods:

α-Melanotropin (MT-II: Ac-Nle-cyclo[Asp-His-D-Phe-Arg-Trp-Lys]-$NH_2$, SEQ ID NO. 91) was obtained as a lyophilized powder manufactured by Innovative Opportunities (Kingwood, Tex. USA). Sodium 8-((2-hydroxybenzoyl) amino) octanoate: (SNAC) was provided by Align Bioscience LLC (223 Vosburgh Pavilion, NYMC, Valhalla, N.Y. 10595). Trypsin inhibitor from *Glycine max* (soybean) (SBTI) was purchased from Sigma-Aldrich Company (USA). The water used in experiment was WFIJ. Male Sprague-Dawley rats (SD rat) were purchased from Taconic (Hudson, N.Y. USA) weighing 250-380 g.

LC/Ms/MS Analysis Method:

The blood serums were analyzed by liquid chromatography/tandem mass spectrometry (LC-MS/MS). The LC-MS/MS system was composed of Shimadzu Prominence pumps, SIL-20ACHT auto sampler, and Applied Bio systems/MDS Sciex API 3200 triple quadrupole mass spectrometer. Analytical separation was achieved on a Sepax BR-C18 column (5 μm, 2.1×50 mm).

The 20 μL internal standard solution was added into the serum samples (50 μL); serum samples were purified by protein precipitation method with 150 μL of acetonitrile. The supernatant was injected onto liquid chromatography/tandem mass spectrometry (LC-MS/MS) with electrospray ionization in positive ion mode.

Mobile phase A: with 0.2% ammonia in 10 mM ammonium acetate aqueous solution. Mobile phase B: methanol:water:formic acid 95:5:0.1. A gradient elution started with 30% B and continued to 1 min. From 1 min. to 3 min., mobile phase B percentage increased from 30 to 75. From 3 to 6 min., mobile phase B percentage stayed at 75. From 6 to 10 min., mobile phase B percentage was 100. The column was then equilibrated with 30% B for 1.5 min. The multiple reaction monitoring (MRM) transitions chosen for melanotan II, and propanol were 512.9→86, and 260→155, respectively. The calibration range for melanotan II is 1 to 400 ng/mL.

Experimental Procedure:
Drug Dose Information:
1. SC injection solution: 40 μg/0.1 ml water, 160 μg/kg.
2. Oral tablet: The tablet was prepared at a ratio of 1:20:150 (MT-II: SBTI: SNAC). 800 μg/kg of MT-II. The tablet was prepared by a standard simple mixture method and compression procedure.

General Experimental Procedure:
Sprague-Dawley (SD) rats were dosed either Subcutaneously (SC) for positive control study or orally by dosing syringe after anesthesia treatment using a 2 minute inhalation. Prior to oral experiment, rats were placed in fasting conditions for 12 hr. The animal study was performed according to the institutional requirements and ethical guidelines.

The blood samples were collected by the tail clipping method at the following time points: −0, 15, 30, 45, 60, 120, 180, 240, 300 min. following drug administration. 150 μl per sample was collected in 0.5 ml of centrifuge vials and kept on ice. Samples were then transferred to dry ice, and stored at −20° C. for further blood analysis.

In some embodiments, a method for oral administration of a melanocortin receptor agonist to a subject in need thereof is provided, the method comprising administering orally to the subject a pharmaceutical composition comprising the melanocortin receptor agonist, a protease inhibitor, and an absorption enhancer wherein the absorption enhancer enhances the absorption of the melanocortin receptor through an intestinal mucosal barrier.

In some embodiments, a method for treating sexual dysfunction in a subject in need thereof is provided, the method comprising administering orally to the subject a pharmaceutical composition comprising a melanocortin receptor agonist, a protease inhibitor, and an absorption enhancer wherein the absorption enhancer enhances the absorption of the melanocortin receptor through an intestinal mucosal barrier of the subject.

In some embodiments, a method of treating metabolic syndrome, diabetes, obesity or any combination thereof in a subject in need thereof is provided, the method comprising administering orally to the subject a pharmaceutical composition comprising a melanocortin receptor agonist, a protease inhibitor, and an absorption enhancer wherein the absorption enhancer enhances the absorption of the melanocortin receptor through an intestinal mucosal barrier of the subject.

In some embodiments, a pharmaceutical composition comprising a melanocortin receptor agonist, a protease inhibitor, and an absorption enhancer is provided, wherein the absorption enhancer is capable of enhancing absorption of the melanocortin receptor through an intestinal mucosal barrier.

The foregoing specific embodiments represent just some of the ways of practicing the present invention. Many other embodiments are possible within the spirit of the invention. Accordingly, the scope of the invention is not limited to the foregoing specification, but instead is given by the appended claims along with their full range of equivalents.

What is claimed is:

1. A method for oral administration of a melanocortin receptor agonist to a subject in need thereof comprising administering orally to the subject a pharmaceutical composition comprising the melanocortin receptor agonist, a protease inhibitor, and an absorption enhancer wherein the absorption enhancer enhances the absorption of the melanocortin receptor through an intestinal mucosal barrier, wherein the absorption enhancer is N-(8-[2-hydroxybenzoyl] amino)caprylate (SNAC), Sodium N-(10-[2-hydroxybenzoyl]amino)decanoate (SNAD), pharmaceutical salts thereof or a combination thereof.

2. A method for oral administration of a melanocortin receptor agonist to a subject in need thereof comprising administering orally to the subject a pharmaceutical composition comprising the melanocortin receptor agonist, a protease inhibitor, and an absorption enhancer wherein the absorption enhancer enhances the absorption of the melanocortin receptor through an intestinal mucosal barrier, wherein in the step of administering the pharmaceutical composition further comprises an omega-3 fatty acid, EDTA or a salt thereof, and an antiemetic compound.

* * * * *

SEQUENCE LISTING

```
<160> NUMBER OF SEQ ID NOS: 133

<210> SEQ ID NO 1
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 1

Ser Tyr Ser Met Glu His Phe Arg Trp Gly Lys Pro Val
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Met Glu His Phe Arg Trp Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic construct

<400> SEQUENCE: 3

His Phe Arg Trp
```

<210> SEQ ID NO 4
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: D-Phe

<400> SEQUENCE: 4

His Phe Arg Trp
1

<210> SEQ ID NO 5
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: DEAMINATION

<400> SEQUENCE: 5

Ser Tyr Ser Met Glu His Phe Arg Trp Gly Lys Pro Val
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: D-Phe

<400> SEQUENCE: 6

Ser Tyr Ser Met Glu His Phe Arg Trp Gly Lys Pro Val
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (13)..(13)

```
<223> OTHER INFORMATION: DEAMINATION

<400> SEQUENCE: 7

Ser Tyr Ser Met Glu His Phe Arg Trp Gly Lys Pro Val
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: X is Met, Nle, or Cys
<220> FEATURE:
<221> NAME/KEY: MOD_RES
<222> LOCATION: (7)..(7)
<223> OTHER INFORMATION: D-Phe

<400> SEQUENCE: 8

Ser Tyr Ser Xaa Glu His Phe Arg Trp Gly Lys Pro Val
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe

<400> SEQUENCE: 9

Xaa Asp His Phe Arg Trp Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: DEAMINATION

<400> SEQUENCE: 10

Xaa Asp His Phe Arg Trp Lys
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 11

Met Glu His Phe Arg Trp Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe

<400> SEQUENCE: 12

Xaa Asp His Phe Arg Trp
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION, X is Nle
<220> FEATURE:
<221> NAME/KEY: MOD_RES
<222> LOCATION: (4)..(4)
<223> OTHER INFORMATION: D-Phe

<400> SEQUENCE: 13

Xaa Asp His Phe Arg Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 14

Met Glu His Phe Arg Trp Gly Lys
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION, X is Nle

<400> SEQUENCE: 15

Xaa Glu His Phe Arg Trp Gly Lys
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: D-Phe

<400> SEQUENCE: 16

Met Glu His Phe Arg Trp Gly Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION, X is Nle
<220> FEATURE:
<221> NAME/KEY: MOD_RES
<222> LOCATION: (4)..(4)
<223> OTHER INFORMATION: D-Phe

<400> SEQUENCE: 17

Xaa Glu His Phe Arg Trp Gly Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: AMIDATION
<220> FEATURE:
<221> NAME/KEY: MOD_RES
<222> LOCATION: (4)..(4)
<223> OTHER INFORMATION: p-nitro-D-Phe

<400> SEQUENCE: 18

Met Glu His Phe Arg Trp Gly Lys
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION; X is Nle
<220> FEATURE:
<221> NAME/KEY: MOD_RES
<222> LOCATION: (4)..(4)
<223> OTHER INFORMATION: D-Phe

<400> SEQUENCE: 19

Xaa Glu His Phe Arg Trp Gly Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: D-Phe

<400> SEQUENCE: 20

Tyr Glu His Phe Arg Trp Gly Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION; X is Nle
<220> FEATURE:
<221> NAME/KEY: MOD_RES
<222> LOCATION: (4)..(4)
<223> OTHER INFORMATION: p-nitro-D-Phe

<400> SEQUENCE: 21

Xaa Glu His Phe Arg Trp Gly Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION; X is Nle
<220> FEATURE:
<221> NAME/KEY: MOD_RES
<222> LOCATION: (5)..(5)
<223> OTHER INFORMATION: D-Arg
```

<400> SEQUENCE: 22

Xaa Glu His Phe Arg Trp Gly Lys
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION; X is Nle
<220> FEATURE:
<221> NAME/KEY: MOD_RES
<222> LOCATION: (6)..(6)
<223> OTHER INFORMATION: D-Trp

<400> SEQUENCE: 23

Xaa Glu His Phe Arg Trp Gly Lys
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION; X is Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 24

Xaa Glu His Phe Arg Trp Gly Lys
1               5

<210> SEQ ID NO 25
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Met or Nle
<220> FEATURE:
<221> NAME/KEY: MOD_RES
<222> LOCATION: (7)..(7)
<223> OTHER INFORMATION: D-Phe

<400> SEQUENCE: 25

Ser Tyr Ser Xaa Glu His Xaa Arg Trp Gly Lys Pro Val
1               5                   10

<210> SEQ ID NO 26

```
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (7)..(7)
<223> OTHER INFORMATION: D-Phe

<400> SEQUENCE: 26

Ser Tyr Ser Met Glu His Phe Arg Trp Gly Lys Pro Val
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (7)..(7)
<223> OTHER INFORMATION: D-Phe

<400> SEQUENCE: 27

Ser Tyr Ser Met Glu His Phe Arg Trp Gly Lys Pro Val
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (3)..(3)
<223> OTHER INFORMATION: D-Ser
<220> FEATURE:
<221> NAME/KEY: MOD_RES
<222> LOCATION: (7)..(7)
<223> OTHER INFORMATION: D-Phe

<400> SEQUENCE: 28

Ser Tyr Ser Met Glu His Phe Arg Trp Gly Lys Pro Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (4)..(4)
<223> OTHER INFORMATION: D-Met
<220> FEATURE:
<221> NAME/KEY: MOD_RES
<222> LOCATION: (7)..(7)
<223> OTHER INFORMATION: D-Phe

<400> SEQUENCE: 29
```

Ser Tyr Ser Met Glu His Phe Arg Trp Gly Lys Pro Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (7)..(7)
<223> OTHER INFORMATION: D-Phe

<400> SEQUENCE: 30

Ser Tyr Ser Met Glu His Phe Arg Trp Gly Lys Pro Val
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Phe

<400> SEQUENCE: 31

Ser Tyr Ser Met Glu His Phe Arg Trp Gly Lys Pro Val
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: D-Arg

<400> SEQUENCE: 32

Ser Tyr Ser Met Glu His Phe Arg Trp Gly Lys Pro Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (9)..(9)
<223> OTHER INFORMATION: D-Trp

<400> SEQUENCE: 33

Ser Tyr Ser Met Glu His Phe Arg Trp Gly Lys Pro Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (11)..(11)
<223> OTHER INFORMATION: D-Lys

<400> SEQUENCE: 34

Ser Tyr Ser Met Glu His Phe Arg Trp Gly Lys Pro Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (12)..(12)
<223> OTHER INFORMATION: D-Pro

<400> SEQUENCE: 35

Ser Tyr Ser Met Glu His Phe Arg Trp Gly Lys Pro Val
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: D-Val

<400> SEQUENCE: 36

Ser Tyr Ser Met Glu His Phe Arg Trp Gly Lys Pro Val
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic construct
<220> FEATURE:

```
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe

<400> SEQUENCE: 37

Ser Tyr Ser Xaa Glu His Phe Arg Trp Gly Lys Pro Val
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe

<400> SEQUENCE: 38

Ser Tyr Ser Xaa Glu His Phe Arg Trp Gly Lys Pro Val
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe

<400> SEQUENCE: 39

Ser Tyr Ser Xaa Glu His Phe Arg Trp Gly Lys Pro Val
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
```

```
<221> NAME/KEY: MOD_RES
<222> LOCATION: (4)..(4)
<223> OTHER INFORMATION: X is Nle
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (7)..(7)
<223> OTHER INFORMATION: D-Phe

<400> SEQUENCE: 40

Xaa Tyr Ser Met Glu His Phe Arg Trp Gly Lys Pro Val
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (4)..(4)
<223> OTHER INFORMATION: X is Nle
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Phe

<400> SEQUENCE: 41

Ser Tyr Ser Xaa Glu His Phe Arg Trp Gly Lys Pro Val
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: D-Arg

<400> SEQUENCE: 42

Ser Tyr Ser Xaa Glu His Phe Arg Trp Gly Lys Pro Val
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X is Nle
<220> FEATURE:
```

```
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (9)..(9)
<223> OTHER INFORMATION: D-Trp

<400> SEQUENCE: 43

Ser Tyr Ser Xaa Glu His Phe Arg Trp Gly Lys Pro Val
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (11)..(11)
<223> OTHER INFORMATION: D-Lys

<400> SEQUENCE: 44

Ser Tyr Ser Xaa Glu His Phe Arg Trp Gly Lys Pro Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (12)..(12)
<223> OTHER INFORMATION: D-Pro

<400> SEQUENCE: 45

Ser Tyr Ser Xaa Glu His Phe Arg Trp Gly Lys Pro Val
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe
<220> FEATURE:
```

```
<221> NAME/KEY: MOD_RES
<222> LOCATION: (13)..(13)
<223> OTHER INFORMATION: D-Val

<400> SEQUENCE: 46

Ser Tyr Ser Xaa Glu His Phe Arg Trp Gly Lys Pro Val
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is Glu or Asp
<220> FEATURE:
<221> NAME/KEY: MISC_FEATURE
<222> LOCATION: (4)..(4)
<223> OTHER INFORMATION: X is Phe or D-Phe
<220> FEATURE:
<221> NAME/KEY: MISC_FEATURE
<222> LOCATION: (7)..(7)
<223> OTHER INFORMATION: X is Lys, Orn, Dbu or Dpr

<400> SEQUENCE: 47

Xaa Xaa His Xaa Arg Trp Xaa
1               5

<210> SEQ ID NO 48
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe

<400> SEQUENCE: 48

Ser Tyr Ser Xaa Glu His Phe Arg Trp Lys Gly Pro Val
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (4)..(4)
<223> OTHER INFORMATION: X is Nle
<220> FEATURE:
<221> NAME/KEY: MOD_RES
<222> LOCATION: (7)..(7)
<223> OTHER INFORMATION: D-Phe

<400> SEQUENCE: 49

Ser Tyr Ser Xaa Asp His Phe Arg Trp Lys Gly Pro Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe

<400> SEQUENCE: 50

Xaa Glu His Phe Arg Trp Lys Gly Pro Val
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe

<400> SEQUENCE: 51

Xaa Asp His Phe Arg Trp Gly
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (4)..(4)
<223> OTHER INFORMATION: D-Phe

<400> SEQUENCE: 52

Xaa Asp His Phe Arg Trp Lys
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: X is Orn

<400> SEQUENCE: 53

Xaa Asp His Phe Arg Trp Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: X is Orn

<400> SEQUENCE: 54

Xaa Glu His Phe Arg Trp Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MISC_FEATURE
<222> LOCATION: (7)..(7)
<223> OTHER INFORMATION: X is Dbu

<400> SEQUENCE: 55

Xaa Glu His Phe Arg Trp Xaa
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: X is Dbu

<400> SEQUENCE: 56

Xaa Asp His Phe Arg Trp Xaa
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: X is Dpr or Dbu

<400> SEQUENCE: 57

Xaa Asp His Phe Arg Trp Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: X is Dbu

<400> SEQUENCE: 58

Xaa Glu His Phe Arg Trp Xaa
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Acetylated Ser, or Tyr-Ser
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is Nle
<220> FEATURE:
<221> NAME/KEY: MISC_FEATURE
<222> LOCATION: (3)..(3)
<223> OTHER INFORMATION: X is Glu or Asp
<220> FEATURE:
<221> NAME/KEY: MISC_FEATURE
<222> LOCATION: (5)..(5)
<223> OTHER INFORMATION: X is Phe, D-Phe, Arg, or Trp
<220> FEATURE:
<221> NAME/KEY: MISC_FEATURE
<222> LOCATION: (8)..(8)
<223> OTHER INFORMATION: X is Lys, Gly, Orn, Dub or Dpr
<220> FEATURE:
<221> NAME/KEY: MISC_FEATURE
<222> LOCATION: (9)..(9)
<223> OTHER INFORMATION: X is Gly-Val, Pro, deaminated Gly-Val,
      deaminated Pro
<220> FEATURE:
<221> NAME/KEY: MISC_FEATURE
<222> LOCATION: (9)..(9)
<223> OTHER INFORMATION: X can be present or absent, NH2, OH, Gly-Val,
      Pro, deaminated Gly-Val, deaminated Pro

<400> SEQUENCE: 59

Xaa Xaa Xaa His Xaa Arg Trp Xaa Xaa
1               5

<210> SEQ ID NO 60
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (4)..(10)
<223> OTHER INFORMATION: cyclic bridge
```

```
<400> SEQUENCE: 60

Ser Tyr Ser Cys Glu His Phe Arg Trp Cys Lys Pro Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: Cyclic bridge

<400> SEQUENCE: 61

Cys Glu His Phe Arg Trp Cys Lys Pro Val
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (4)..(11)
<223> OTHER INFORMATION: cyclic bridge

<400> SEQUENCE: 62

Ser Tyr Ser Cys Glu His Phe Arg Trp Gly Cys Pro Val
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(8)
<223> OTHER INFORMATION: cyclic bridge

<400> SEQUENCE: 63

Cys Glu His Phe Arg Trp Gly Cys Pro Val
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (5)..(10)
<223> OTHER INFORMATION: cyclic bridge

<400> SEQUENCE: 64

Ser Tyr Ser Met Cys His Phe Arg Trp Cys Lys Pro Val
1               5                   10

<210> SEQ ID NO 65
<211> LENGTH: 9
<212> TYPE: PRT
<213> ORGANISM: Artificial Sequence
```

```
<220> FEATURE:
<223> OTHER INFORMATION: Synthetic construct
<220> FEATURE:
<221> NAME/KEY: DISULFID
<222> LOCATION: (1)..(6)
<223> OTHER INFORMATION: cyclic bridge

<400> SEQUENCE: 65

Cys His Phe Arg Trp Cys Lys Pro Val
1               5

<210> SEQ ID NO 66
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (5)..(11)
<223> OTHER INFORMATION: cyclic bridge

<400> SEQUENCE: 66

Ser Tyr Ser Met Cys His Phe Arg Trp Gly Cys Pro Val
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: cyclic bridge

<400> SEQUENCE: 67

Cys His Phe Arg Trp Gly Cys Pro Val
1               5

<210> SEQ ID NO 68
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (4)..(10)
<223> OTHER INFORMATION: cyclic bridge
<220> FEATURE:
<221> NAME/KEY: DISULFID
<222> LOCATION: (5)..(11)
<223> OTHER INFORMATION: cyclic bridge

<400> SEQUENCE: 68

Ser Tyr Ser Cys Cys His Phe Arg Trp Cys Cys Pro Val
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: cyclic bridge
<220> FEATURE:
```

```
<221> NAME/KEY: DISULFID
<222> LOCATION: (2)..(8)
<223> OTHER INFORMATION: cyclic bridge

<400> SEQUENCE: 69

Cys Cys His Phe Arg Trp Cys Cys Pro Val
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (4)..(11)
<223> OTHER INFORMATION: cyclic bridge
<220> FEATURE:
<221> NAME/KEY: DISULFID
<222> LOCATION: (5)..(10)
<223> OTHER INFORMATION: cyclic bridge

<400> SEQUENCE: 70

Ser Tyr Ser Met Glu His Phe Arg Trp Gly Lys Pro Val
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(8)
<223> OTHER INFORMATION: cyclic bridge
<220> FEATURE:
<221> NAME/KEY: DISULFID
<222> LOCATION: (2)..(7)
<223> OTHER INFORMATION: cyclic bridge

<400> SEQUENCE: 71

Cys Cys His Phe Arg Trp Cys Cys Pro Val
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (4)..(10)
<223> OTHER INFORMATION: carba bridge
<220> FEATURE:
<221> NAME/KEY: MISC_FEATURE
<222> LOCATION: (10)..(10)
<223> OTHER INFORMATION: Cys carba analog

<400> SEQUENCE: 72

Ser Tyr Ser Cys Glu His Phe Arg Trp Cys Lys Pro Val
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (4)..(11)
<223> OTHER INFORMATION: Carba bridge
<220> FEATURE:
<221> NAME/KEY: MISC_FEATURE
<222> LOCATION: (11)..(11)
<223> OTHER INFORMATION: Cys carba analog

<400> SEQUENCE: 73

Ser Tyr Ser Cys Glu His Phe Arg Trp Gly Cys Pro Val
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(10)
<223> OTHER INFORMATION: Carba bridge
<220> FEATURE:
<221> NAME/KEY: MISC_FEATURE
<222> LOCATION: (10)..(10)
<223> OTHER INFORMATION: Cys carba analog

<400> SEQUENCE: 74

Ser Tyr Ser Met Cys His Phe Arg Trp Cys Lys Pro Val
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(11)
<223> OTHER INFORMATION: carba bridge
<220> FEATURE:
<221> NAME/KEY: MISC_FEATURE
<222> LOCATION: (11)..(11)
<223> OTHER INFORMATION: Cys carba analog

<400> SEQUENCE: 75

Ser Tyr Ser Met Cys His Phe Arg Trp Gly Cys Pro Val
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(10)
<223> OTHER INFORMATION: Carba bridge
<220> FEATURE:
<221> NAME/KEY: MISC_FEATURE
<222> LOCATION: (4)..(4)
<223> OTHER INFORMATION: Cys carba analog

<400> SEQUENCE: 76

Ser Tyr Ser Cys Glu His Phe Arg Trp Cys Lys Pro Val
1               5                   10

<210> SEQ ID NO 77
```

<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(10)
<223> OTHER INFORMATION: carba bond
<220> FEATURE:
<221> NAME/KEY: MISC_FEATURE
<222> LOCATION: (5)..(5)
<223> OTHER INFORMATION: Cys carba analog

<400> SEQUENCE: 77

Ser Tyr Ser Met Cys His Phe Arg Trp Cys Lys Pro Val
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(11)
<223> OTHER INFORMATION: Carba bridge
<220> FEATURE:
<221> NAME/KEY: MISC_FEATURE
<222> LOCATION: (4)..(4)
<223> OTHER INFORMATION: Cys carba analog

<400> SEQUENCE: 78

Ser Tyr Ser Cys Glu His Phe Arg Trp Gly Cys Pro Val
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(10)
<223> OTHER INFORMATION: Carba bridge
<220> FEATURE:
<221> NAME/KEY: MISC_FEATURE
<222> LOCATION: (5)..(5)
<223> OTHER INFORMATION: Cys carba analog

<400> SEQUENCE: 79

Ser Tyr Ser Met Cys His Phe Arg Trp Gly Cys Pro Val
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(10)
<223> OTHER INFORMATION: carba bridge
<220> FEATURE:
<221> NAME/KEY: MISC_FEATURE
<222> LOCATION: (4)..(4)
<223> OTHER INFORMATION: Cys carba analog
<220> FEATURE:
<221> NAME/KEY: MISC_FEATURE
<222> LOCATION: (10)..(10)

<223> OTHER INFORMATION: Cys carba analog

<400> SEQUENCE: 80

Ser Tyr Ser Cys Glu His Phe Arg Trp Cys Lys Pro Val
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(11)
<223> OTHER INFORMATION: Carba bridge
<220> FEATURE:
<221> NAME/KEY: MISC_FEATURE
<222> LOCATION: (4)..(4)
<223> OTHER INFORMATION: Cys carba analog
<220> FEATURE:
<221> NAME/KEY: MISC_FEATURE
<222> LOCATION: (11)..(11)
<223> OTHER INFORMATION: Cys carba analog

<400> SEQUENCE: 81

Ser Tyr Ser Cys Glu His Phe Arg Trp Gly Cys Pro Val
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(10)
<223> OTHER INFORMATION: Carba bridge
<220> FEATURE:
<221> NAME/KEY: MISC_FEATURE
<222> LOCATION: (5)..(5)
<223> OTHER INFORMATION: Cys carba analog
<220> FEATURE:
<221> NAME/KEY: MISC_FEATURE
<222> LOCATION: (10)..(10)
<223> OTHER INFORMATION: Cys carba analog

<400> SEQUENCE: 82

Ser Tyr Ser Met Cys His Phe Arg Trp Cys Lys Pro Val
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(11)
<223> OTHER INFORMATION: Carba bridge
<220> FEATURE:
<221> NAME/KEY: MISC_FEATURE
<222> LOCATION: (5)..(5)
<223> OTHER INFORMATION: Cys carba analog
<220> FEATURE:
<221> NAME/KEY: MISC_FEATURE
<222> LOCATION: (11)..(11)
<223> OTHER INFORMATION: Cys carba analog

<400> SEQUENCE: 83

Ser Tyr Ser Met Glu His Phe Arg Trp Gly Lys Pro Val
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(10)
<223> OTHER INFORMATION: Carba bridge
<220> FEATURE:
<221> NAME/KEY: MISC_FEATURE
<222> LOCATION: (4)..(4)
<223> OTHER INFORMATION: Cys carba analog
<220> FEATURE:
<221> NAME/KEY: MISC_FEATURE
<222> LOCATION: (5)..(11)
<223> OTHER INFORMATION: Carba bridge
<220> FEATURE:
<221> NAME/KEY: MISC_FEATURE
<222> LOCATION: (5)..(5)
<223> OTHER INFORMATION: Cys carba analog
<220> FEATURE:
<221> NAME/KEY: MISC_FEATURE
<222> LOCATION: (10)..(10)
<223> OTHER INFORMATION: Cys carba analog
<220> FEATURE:
<221> NAME/KEY: MISC_FEATURE
<222> LOCATION: (11)..(11)
<223> OTHER INFORMATION: Cys carba analog

<400> SEQUENCE: 84

Ser Tyr Ser Cys Cys His Phe Arg Trp Cys Cys Pro Val
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(11)
<223> OTHER INFORMATION: Carba bridge
<220> FEATURE:
<221> NAME/KEY: MISC_FEATURE
<222> LOCATION: (4)..(4)
<223> OTHER INFORMATION: Cys carba analog
<220> FEATURE:
<221> NAME/KEY: MISC_FEATURE
<222> LOCATION: (5)..(10)
<223> OTHER INFORMATION: Carba bridge
<220> FEATURE:
<221> NAME/KEY: MISC_FEATURE
<222> LOCATION: (5)..(5)
<223> OTHER INFORMATION: Cys carba analog
<220> FEATURE:
<221> NAME/KEY: MISC_FEATURE
<222> LOCATION: (10)..(10)
<223> OTHER INFORMATION: Cys carba analog
<220> FEATURE:
<221> NAME/KEY: MISC_FEATURE
<222> LOCATION: (11)..(11)
<223> OTHER INFORMATION: Cys carba analog

<400> SEQUENCE: 85

Ser Tyr Ser Cys Cys His Phe Arg Trp Cys Cys Pro Val
1               5                   10

<210> SEQ ID NO 86

```
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (7)..(7)
<223> OTHER INFORMATION: deamination

<400> SEQUENCE: 86

Cys Glu His Phe Lys Trp Cys
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (7)..(7)
<223> OTHER INFORMATION: deamination

<400> SEQUENCE: 87

Cys Glu His Phe Lys Phe Cys
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (7)..(7)
<223> OTHER INFORMATION: D-Cys

<400> SEQUENCE: 88

Cys Glu His Phe Arg Trp Cys
1               5

<210> SEQ ID NO 89
<211> LENGTH: 7
<212> TYPE: PRT
<213> ORGANISM: Artificial Sequence
<220> FEATURE:
```

```
<223> OTHER INFORMATION: Synthetic construct
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (7)..(7)
<223> OTHER INFORMATION: D-Cys
<220> FEATURE:
<221> NAME/KEY: MOD_RES
<222> LOCATION: (7)..(7)
<223> OTHER INFORMATION: deamination

<400> SEQUENCE: 89

Cys Glu His Phe Lys Phe Cys
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (7)..(7)
<223> OTHER INFORMATION: D-Cys
<220> FEATURE:
<221> NAME/KEY: MOD_RES
<222> LOCATION: (7)..(7)
<223> OTHER INFORMATION: deamination

<400> SEQUENCE: 90

Cys Glu His Phe Lys Trp Cys
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 91

Xaa Asp His Phe Arg Trp Lys
```

-continued

```
<210> SEQ ID NO 92
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 92

Xaa Asp His Phe Arg Trp Lys Gly
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 93

Xaa Asp His Phe Arg Trp Lys Gly Pro
1               5

<210> SEQ ID NO 94
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: X is Nle
<220> FEATURE:
<221> NAME/KEY: MISC_FEATURE
<222> LOCATION: (5)..(10)
<223> OTHER INFORMATION: cyclic peptide
```

```
<220> FEATURE:
<221> NAME/KEY: MOD_RES
<222> LOCATION: (7)..(7)
<223> OTHER INFORMATION: D-Phe

<400> SEQUENCE: 94

Ser Tyr Ser Xaa Asp His Phe Arg Trp Lys
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is Nle
<220> FEATURE:
<221> NAME/KEY: MISC_FEATURE
<222> LOCATION: (3)..(8)
<223> OTHER INFORMATION: cyclic peptide
<220> FEATURE:
<221> NAME/KEY: MOD_RES
<222> LOCATION: (5)..(5)
<223> OTHER INFORMATION: D-Phe

<400> SEQUENCE: 95

Ser Xaa Asp His Phe Arg Trp Lys
1               5

<210> SEQ ID NO 96
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(10)
<223> OTHER INFORMATION: cyclic peptide
<220> FEATURE:
<221> NAME/KEY: MOD_RES
<222> LOCATION: (7)..(7)
<223> OTHER INFORMATION: D-Phe

<400> SEQUENCE: 96

Ser Tyr Ser Cys Glu His Phe Arg Trp Cys Lys Pro Val
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
```

```
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-phe

<400> SEQUENCE: 97

Xaa Asp His Phe Arg Trp Lys
1               5

<210> SEQ ID NO 98
<211> LENGTH: 12
<212> TYPE: PRT
<213> ORGANISM: Artificial Sequence
<220> FEATURE:
<223> OTHER INFORMATION: Synthetic construct

<400> SEQUENCE: 98

Ser Tyr Ser Met Glu His Phe Arg Trp Gly Lys Pro
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic construct

<400> SEQUENCE: 99

Ser Tyr Ser Met Glu His Phe Arg Trp Gly Lys
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic construct

<400> SEQUENCE: 100

Met Glu His Phe Arg Trp Gly Lys Pro Val
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (4)..(10)
<223> OTHER INFORMATION: disulfide bridge

<400> SEQUENCE: 101

Ser Tyr Ser Cys Glu His Phe Arg Trp Cys Lys Pro Val
1               5                   10

<210> SEQ ID NO 102
<211> LENGTH: 10
<212> TYPE: PRT
<213> ORGANISM: Artificial Sequence
```

```
<220> FEATURE:
<223> OTHER INFORMATION: Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (4)..(4)
<223> OTHER INFORMATION: D-Phe

<400> SEQUENCE: 102

Cys Glu His Phe Arg Trp Cys Lys Pro Val
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: disulfide bridge

<400> SEQUENCE: 103

Cys Glu His Phe Arg Trp Cys Lys Pro
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D-Phe
<220> FEATURE:
<221> NAME/KEY: DISULFID
<222> LOCATION: (1)..(7)
<223> OTHER INFORMATION: disulfide bridge

<400> SEQUENCE: 104

Cys Glu His Phe Arg Trp Cys Lys Pro
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
```

```
<222> LOCATION: (4)..(7)
<223> OTHER INFORMATION: disulfide bridge

<400> SEQUENCE: 105

Met Glu His Phe Arg Trp Gly Lys
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (4)..(4)
<223> OTHER INFORMATION: D-Phe

<400> SEQUENCE: 106

Met Glu His Phe Arg Trp Gly Lys
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(7)
<223> OTHER INFORMATION: disulfide bridge

<400> SEQUENCE: 107

Cys Glu His Phe Arg Trp Cys
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (4)..(4)
<223> OTHER INFORMATION: D-Phe

<400> SEQUENCE: 108

Cys Glu His Phe Arg Trp Cys
1               5
```

```
<210> SEQ ID NO 109
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: disulfide bridge
<220> FEATURE:
<221> NAME/KEY: MOD_RES
<222> LOCATION: (4)..(4)
<223> OTHER INFORMATION: D-Phe

<400> SEQUENCE: 109

Cys Glu His Phe Arg Trp Cys Lys
1               5

<210> SEQ ID NO 110
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MISC_FEATURE
<222> LOCATION: (1)..(1)
<223> OTHER INFORMATION: X is Mpa

<400> SEQUENCE: 110

Xaa Glu His Phe Arg Trp Cys Lys Pro Val
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MISC_FEATURE
<222> LOCATION: (1)..(1)
<223> OTHER INFORMATION: X is Maa

<400> SEQUENCE: 111

Xaa Glu His Phe Arg Trp Cys Lys Pro Val
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: cyclic peptide
<220> FEATURE:
```

```
<221> NAME/KEY: MISC_FEATURE
<222> LOCATION: (1)..(1)
<223> OTHER INFORMATION: X is Hcy
<220> FEATURE:
<221> NAME/KEY: MOD_RES
<222> LOCATION: (1)..(1)
<223> OTHER INFORMATION: ACETYLATION

<400> SEQUENCE: 112

Xaa Glu His Phe Arg Trp Cys Lys Pro Val
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 113

Xaa Asp His Phe Arg Trp Lys
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MISC_FEATURE
<222> LOCATION: (2)..()
<223> OTHER INFORMATION: Cyclic peptide
<220> FEATURE:
<221> NAME/KEY: MISC_FEATURE
<222> LOCATION: (4)..(4)
<223> OTHER INFORMATION: X is have D-2'-naphtalanine

<400> SEQUENCE: 114

Xaa Asn His Xaa Arg Trp Lys
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MISC_FEATURE
<222> LOCATION: (4)..(4)
<223> OTHER INFORMATION: X is D-para-iodo-phenylalanine

<400> SEQUENCE: 115

Xaa Asn His Xaa Arg Trp Lys
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MOD_RES
<222> LOCATION: (6)..(6)
<223> OTHER INFORMATION: METHYLATION

<400> SEQUENCE: 116

Asp His Phe Arg Trp Lys
1               5

<210> SEQ ID NO 117
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MOD_RES
<222> LOCATION: (6)..(6)
<223> OTHER INFORMATION: Addition of CH2-CH3

<400> SEQUENCE: 117

Asn His Phe Arg Trp Lys
1               5
```

```
<210> SEQ ID NO 118
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MISC_FEATURE
<222> LOCATION: (5)..(5)
<223> OTHER INFORMATION: X is Nal1
<220> FEATURE:
<221> NAME/KEY: MOD_RES
<222> LOCATION: (6)..(6)
<223> OTHER INFORMATION: Addition CH2-CH3

<400> SEQUENCE: 118

Asp Trp Phe Arg Xaa Lys
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MISC_FEATURE
<222> LOCATION: (5)..(5)
<223> OTHER INFORMATION: X is Nal1
<220> FEATURE:
<221> NAME/KEY: MOD_RES
<222> LOCATION: (6)..(6)
<223> OTHER INFORMATION: addition (CH3)2

<400> SEQUENCE: 119

Asp Trp Phe Arg Xaa Lys
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
```

```
<222> LOCATION: (1)..(6)
<223> OTHER INFORMATION: cyclic peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MISC_FEATURE
<222> LOCATION: (5)..(5)
<223> OTHER INFORMATION: X is Nal1
<220> FEATURE:
<221> NAME/KEY: MOD_RES
<222> LOCATION: (6)..(6)
<223> OTHER INFORMATION: addition CH2-CH3

<400> SEQUENCE: 120

Asp His Phe Arg Xaa Lys
1               5

<210> SEQ ID NO 121
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MISC_FEATURE
<222> LOCATION: (5)..(5)
<223> OTHER INFORMATION: X is Nal1
<220> FEATURE:
<221> NAME/KEY: MOD_RES
<222> LOCATION: (6)..(6)
<223> OTHER INFORMATION: addition (CH3)2

<400> SEQUENCE: 121

Asp His Phe Arg Xaa Lys
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MISC_FEATURE
<222> LOCATION: (2)..(7)
<223> OTHER INFORMATION: cyclic peprtide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

<223> OTHER INFORMATION: Addition CH2-CH3

<400> SEQUENCE: 122

Xaa Asn His Phe Arg Trp Lys
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (7)..(7)
<223> OTHER INFORMATION: Addition (CH3)2

<400> SEQUENCE: 123

Xaa Asp His Phe Arg Trp Lys
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: X is Nal1
<220> FEATURE:
<221> NAME/KEY: MOD_RES
<222> LOCATION: (7)..(7)
<223> OTHER INFORMATION: Addition CH2-CH3

<400> SEQUENCE: 124

Xaa Asp His Phe Arg Xaa Lys
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: X is Nal1
<220> FEATURE:
<221> NAME/KEY: MOD_RES
<222> LOCATION: (7)..(7)
<223> OTHER INFORMATION: Addition (CH3)2

<400> SEQUENCE: 125

Xaa Asp Trp Phe Arg Xaa Lys
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: X is Nal1
<220> FEATURE:
<221> NAME/KEY: MOD_RES
<222> LOCATION: (7)..(7)
<223> OTHER INFORMATION: Addition CH2-CH3

<400> SEQUENCE: 126

Xaa Asp His Phe Arg Xaa Lys
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X is Nle
```

```
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: X is Nal1
<220> FEATURE:
<221> NAME/KEY: MOD_RES
<222> LOCATION: (7)..(7)
<223> OTHER INFORMATION: Addition CH2-CH3

<400> SEQUENCE: 127

Xaa Asn Trp Phe Arg Xaa Lys
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic construct

<400> SEQUENCE: 128

Met Glu His Phe Arg Trp Gly Lys
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic construct

<400> SEQUENCE: 129

Glu His Phe Arg Trp Gly Lys
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic construct

<400> SEQUENCE: 130

Met Glu His Phe Arg Trp
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic construct

<400> SEQUENCE: 131

Glu His Phe Arg Trp Gly Lys Pro Val
1               5

<210> SEQ ID NO 132
<211> LENGTH: 13
<212> TYPE: PRT
<213> ORGANISM: Artificial Sequence
```

```
<220> FEATURE:
<223> OTHER INFORMATION: Synthetic construct

<400> SEQUENCE: 132

Ser Tyr Ser Met Glu His Phe Arg Trp Gly Lys Pro Val
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: deamination

<400> SEQUENCE: 133

Xaa Asp His Phe Arg Trp Lys
1               5
```